US011779567B2

(12) United States Patent
Jacobsen

(10) Patent No.: US 11,779,567 B2
(45) Date of Patent: Oct. 10, 2023

(54) METHOD FOR OPTIMIZING 5-HYDROXYTRYPTAMINE FUNCTION IN THE BRAIN FOR THERAPEUTIC PURPOSES

(71) Applicant: Evecxia Therapeutics, Inc., Research Triangle Park, NC (US)

(72) Inventor: Jacob Pade Ramsoe Jacobsen, Durham, NC (US)

(73) Assignee: Evecxia Therapeutics, Inc., Research Triangle Park, NC (US)

(*) Notice: Subject to any disclaimer, the term of this patent is extended or adjusted under 35 U.S.C. 154(b) by 0 days.

(21) Appl. No.: 17/966,646

(22) Filed: Oct. 14, 2022

(65) Prior Publication Data

US 2023/0121229 A1    Apr. 20, 2023

Related U.S. Application Data

(60) Provisional application No. 63/255,647, filed on Oct. 14, 2021.

(51) Int. Cl.
*A61K 31/405*  (2006.01)
*A61K 45/06*  (2006.01)
*A61P 25/24*  (2006.01)
*A61K 9/00*  (2006.01)

(52) U.S. Cl.
CPC .......... *A61K 31/405* (2013.01); *A61K 9/0019* (2013.01); *A61K 45/06* (2013.01); *A61P 25/24* (2018.01)

(58) Field of Classification Search
CPC .... A61K 31/405; A61K 9/0019; A61K 45/06; A61P 25/24
USPC ...................................................... 514/419
See application file for complete search history.

(56) References Cited

U.S. PATENT DOCUMENTS

| | | | |
|---|---|---|---|
| 4,140,755 A | 2/1979 | Sheth et al. | |
| 4,191,184 A | 3/1980 | Carlisle | |
| 4,658,038 A | 4/1987 | Tamir et al. | |
| 4,996,058 A | 2/1991 | Sinnreich | |
| 6,340,475 B2 | 1/2002 | Shell et al. | |
| 6,475,521 B1 | 11/2002 | Timmins et al. | |
| 6,488,962 B1 | 12/2002 | Berner et al. | |
| 6,635,280 B2 | 10/2003 | Shell et al. | |
| 6,723,340 B2 | 4/2004 | Gusler et al. | |
| 6,960,356 B1 | 11/2005 | Talwar et al. | |
| 7,094,427 B2 | 8/2006 | Han et al. | |
| 7,101,912 B2 | 9/2006 | Xiang et al. | |
| 7,438,927 B2 | 10/2008 | Berner et al. | |
| 7,670,619 B2 | 3/2010 | Mihaylov | |
| 7,674,480 B2 | 3/2010 | Fleshner-Barak et al. | |
| 7,765,989 B2 | 8/2010 | Maruyama | |
| 8,771,730 B2 | 7/2014 | Navon et al. | |
| 8,778,396 B2 | 7/2014 | Pillay et al. | |
| 8,969,400 B2 | 3/2015 | Jacobsen et al. | |
| 9,161,911 B2 | 10/2015 | Hou | |
| 9,468,627 B2 * | 10/2016 | Jacobsen | A61K 9/7023 |
| 9,980,903 B2 | 5/2018 | Berner et al. | |
| 11,337,963 B2 | 5/2022 | Jacobsen et al. | |
| 2006/0013875 A1 | 1/2006 | Han et al. | |
| 2008/0268045 A1 | 10/2008 | Dervieux et al. | |
| 2011/0287096 A1 | 11/2011 | Gorukanti et al. | |
| 2013/0230577 A1 | 9/2013 | Jacobsen et al. | |
| 2017/0266112 A1 | 9/2017 | Bellinger et al. | |
| 2018/0311154 A1 | 11/2018 | Kanasty et al. | |
| 2021/0361566 A1 | 11/2021 | Jacobsen et al. | |
| 2023/0047338 A1 | 2/2023 | Jacobsen et al. | |

FOREIGN PATENT DOCUMENTS

| | | |
|---|---|---|
| CN | 103554005 A | 11/2013 |
| EP | 1382331 A1 | 1/2004 |
| WO | WO 1991/07960 | 6/1991 |
| WO | WO 2004/028512 A1 | 4/2004 |
| WO | WO 2008/100107 A1 | 8/2008 |
| WO | WO 2011/151708 A1 | 12/2011 |
| WO | WO 2019/148087 A1 | 8/2019 |
| WO | WO 2019/245925 A1 | 12/2019 |
| WO | WO2020/014334 A1 | 1/2020 |
| WO | WO 2023/009841 A1 | 2/2023 |
| WO | WO 2023/064598 A1 | 4/2023 |

OTHER PUBLICATIONS

Mashchak et al Journal of clinical endocrinology and metabolism, 1983, vol. 56, pp. 170-176 (Year: 1983).*
Agren et al., "Low brain uptake of L-[11C]5-hydroxytryophan in major depression: a positron emission tomography study on patients and healthy volunteers." Acata Psychiatr. Scand., vol. 83(6), pp. 449-455 (1991).
Alino et al., "5-Hydroxytrytophan (5-HTP) and a MAOI (nialamide) in the treatment of depressions. A double-blind controlled study." Int. Pharmacopsychiatry, vol. 11(1), pp. 8-15 (1976).
Allen GF, Land JM, Heales SJ (2009) "A new perspective on the treatment of aromatic L-amino acid decarboxylase deficiency," Mol Genet Metab 97(1): 6-14.
Appleby et al., "A controlled study of fluoxetine and cognitive-behavioral counselling in the treatment of postnatal depression." Bmj, vol. 314, pp. 932-936 (1997).

(Continued)

*Primary Examiner* — Yevgeny Valenrod
(74) *Attorney, Agent, or Firm* — Jenkins, Taylor & Hunt, P.A.

(57) ABSTRACT

Disclosed herein are methods of elevating brain extracellular 5-hydroxytryptamine ($5\text{-}HT_{Ext}$) and of treating psychiatric conditions and neurological disorders using continuous intravenous infusion of 5-hydroxytryptophan (5-HTP). The methods can be provided for treatment of acute suicidal ideation and/or acute worsening of a mood disorder. The methods can provide rapid onset of therapeutic effect while also having low incidence of acute or moderate adverse effects. Also described herein are compositions for use in the methods, including stable 5-HTP compositions for use in preparing infusate solutions.

22 Claims, 4 Drawing Sheets

(56) References Cited

OTHER PUBLICATIONS

Asberg, "Neurotransmitters and suicidal behavior. The evidence from cerebrospinal fluid studies." Ann. NY Acad. Sci., vol. 836, pp. 158-181 (1997).
Attenburrow et al., (2001). "Low-dose citalopram as a 5-HT neuroendocrine probe," Psychopharmacology 155(3): pp. 323-326.
Badawy et al., "Tryptophan Metabolism in Rat Liver After Administration of Tryptophan, Kynurenine Metabolites, and Kynureninase Inhibitors." Int. J. Tryptophan Res., vol. 9, pp. 51-65 (2016).
Bartels et al., "Impact of SSRI Therapy on Risk of Conversion From Mild Cognitive Impairment to Alzheimer's dementia in Individuals With Previous Depression." Am. J. Psychiatry, vol. 175(3), pp. 232-241 (2018).
Beaulieu et al., "Role of GSK3 beta in behavioral abnormalities induced by serotonin deficiency." Proceedings of the National Academy of Sciences of the United States of America, vol. 105(4), pp. 1333-1338 (2008).
Birdsall et al., "5-Hydroxytryptophan: a clinically-effective serotonin precursor." Altem. Med. Rev., vol. 3(4), pp. 271-280 (1998).
Blier et al., "Current advances and trends in the treatment of depression." Trends in Pharmacological Sciences, vol. 15(7), pp. 220-226 (1994).
Blier et al., "Sequential administration of augmentation strategies in treatment-resistant obsessive-compulsive disorder: preliminary findings." Int. Clin. Psychopharmacol., vol. 11(1), pp. 37-44 (1996).
Bono G, et al. (1984) "L-5HTP treatment in primary headaches: an attempt at clinical identification of responsive patients," Cephalalgia 4(3): 159-165.
Bowsher et al., "Aromatic L-Amino Acid Decarboxylase. In: Boulton et al.," Neurotransmitter Enzymes. Neuromethods, Humana Press, vol. 5, 46 pages (1986).
Brown et al., "Aggression, suicide, and serotonin: relationships to CSF amine metabolites." Am. J. Psychiatry, vol. 139(6), pp. 741-746 (1982).
Bruni et al., "L-5-Hydroxytrytophan treatment of sleep terrors in children." Eur. J. Pediatr., vol. 163(7), pp. 402-407 (2004).
Byerley et al., "5-Hydroxytryptophan: a review of its antidepressant efficacy and adverse effects." J. Clin. Psychopharmacol., vol. 7(3), pp. 127-137 (1987).
Cangiano et al., "Eating behavior and adherence to dietary prescriptions in obese adult subjects treated with 5-hydroxytryptophan." Am. J. Clin. Nutr., vol. 56(5), pp. 863-867 (1993).
Caruso et al., "Double-blind study of 5-Hydroxytryptophan versus placebo in the treatment of primary fibromyalgia syndrome." The Journal of International Medical Research, vol. 18(3), pp. 201-209 (1990).
Carver et al., "Serotonergic function, two-mode models of self-regulation, and vulnerability to depression: what depression has in common with impulsive aggression." Psychol. Bull., vol. 134(6), pp. 912-943 (2008).
Claxton et al., "A systematic review of the associations between dose regimens and medication compliance." Clinical Therapeutics, vol. 23(8), pp. 1296-1310 (2001).
Connor et al., "Fluoxetine in post-traumatic stress disorder." Randomised, double-blind study. Br. J. Psychiatry, vol. 175, pp. 17-22 (1999).
Coric et al., "Multicenter, randomized, double-blind, active comparator and placebo-controlled trial of a corticotropin-releasing factor receptor-1 antagonist in generalized anxiety disorder." Depress. Anxiety, vol. 27(5), pp. 417-425 (2010).
Da Prada et al., "Inhibition of Decarboxylase and Levels of Dopa and 3-O-Methyldopa: A Comparative Study of Benserazide versus Carbidopa in Rodents and of Madopar Standard versus Madopar HBS in Volunteers." Eur. Neurol., vol. 27(Suppl. 1), pp. 9-20 (1987).
Demisch K, et al. (1986) "Melatonin and cortisol increase after fluvoxamine," British journal of clinical pharmacology 22(5): 620-622.
Donnelly, Ronald F (2016) "Stability of Levodopa/Carbidopa Rectal Suspensions," Hosp Pharm. Dec; 51(11): pp. 915-921.
Dulay MS, Dulay JS (2020) "Antiemetics: types, actions and use," Br J Hosp Med (Lond) 81(5): 1-8.
Eisenhofer G et al. (2014) "Levodopa therapy in Parkinson's disease: influence on liquid chromatographic tandem mass spectrometric-based measurements of plasma and urinary normetanephrine, metanephrine and methoxytyramine," Ann Clin Biochem 51(Pt 1): pp. 38-46.
Evecxia therapeutics, Pipeline, May 18, 2021. https://evecxia.com/pipeline/.
Extended European Search Report Corresponding to European Application No. 19823684.6 dated Feb. 23, 2022.
FDA (2022). "Assessing the Effects of Food on Drugs in INDs and NDAs—Clinical Pharmacology Considerations Guidance for Industry," 18 Pages.
Freitas et al., "Novel Levodopa Formulations for Parkinson's Disease." CNS Drugs, vol. 30(11), pp. 1079-1095 (2016).
Fu DJ, et al (2020), "Esketamine Nasal Spray for Rapid Reduction of Major Depressive Disorder Symptoms in Patients Who Have Active Suicidal Ideation With Intent: Double-Blind, Randomized Study (ASPIRE I)," J Clin Psychiatry 81(3), pp. 22-31.
Fuller et al., "Effect of serotonin-releasing drugs on serum corticosterone concentration in rats." Neuroendocrinology, vol. 31(2), pp. 96-100 (1980).
Garfinkel PE, et al. (1977) "The effect of a peripheral decarboxylase inhibitor (carbidopa) on monoamine and neuroendocrine function in man," Neurology 27(5): 443-447.
Gasser et al., "Pharmaceutical quality of seven generic Levodopa/Benserazide products compared with original Madopar®/Prolopa®." BMC Pharmacol. Toxicol., vol. 14, p. 24 (2013).
Gershon, "5-Hydroxytryptamine (serotonin) in the gastrointestinal tract." Curr. Opin. Endocrinol. Diabetes Obes., vol. 20(1), pp. 14-21 (2013).
Gibbons RD et al. (2012) "Suicidal Thoughts and Behavior With Antidepressant Treatment: Reanalysis of the Randomized Placebo-Controlled Studies of Fluoxetine and Venlafaxine," Archives of general psychiatry. 69(6): 15 Pages.
Gijsman et al.,(2002) "Placebo-controlled comparison of three dose-regimens of 5-hydroxytryptophan challenge test in healthy volunteers." J. Clin. Psychopharmacol., vol. 22(2), pp. 183-189.
Guan Z, (2020). "PK/PD modeling of 5-hydroxytryptophan (5-HTP) challenge test with cortisol measurement in serum and saliva" Pharmacol Res Perspect 8(2): e00574.
Guerdjikova et al., High-dose escitalopram in the treatment of binge-eating disorder with obesity: a placebo-controlled monotherapy trial. Hum. Psychopharmacol., vol. 23(1), pp. 1-11 (2008).
Haahr ME, et al (2014) "Central 5-HT4 receptor binding as biomarker of serotonergic tonus in humans: a [11C]SB207145 PET study," Mol Psychiatry 19(4): 427-432.
Haddad, P (1998) The SSRI discontinuation syndrome. J Psychopharmacol. 12(3):305-13.
Hsu et al.,(2015) "Comparison of the pharmacokinetics of an oral extended-release capsule formulation of carbidopa-levodopa (IPX066) with immediate-release carbidopa-levodopa (Sinemet®), sustained-release carbidopa-levodopa (Sinemet® CR), and carbide-levodopa-entacapone (Stalveto®)." Journal of Clinical Pharmacol., pp. 995-1003.
Hua et al., "Advances in oral nano-delivery systems for colon targeted drug delivery in inflammatory bowel disease: selective targeting to diseased versus healthy tissue." Nanomedicine, vol. 11(5), pp. 1117-1132 (2015).
International Preliminary Report on Patentability Corresponding to International application No. PCT/US 2019/037349 dated Dec. 22, 2020.
International Search Report and Written Opinion corresponding to US. Patent application No. PCT/US2022/038914 dated Nov. 22, 2022.
International Search report and Written Opinion of the international searching Authority corresponding to PCT/US 2022/046782 dated Jan. 18, 2023.
International Search Report and Written Opinion of the International Searching Authority Corresponding to International application No. PCT/US 2019/037349 dated Aug. 27, 2019.

(56) References Cited

OTHER PUBLICATIONS

Jackson et al., "Pharmacotherapy of eating disorders." Nutr. Clin. Pract., vol. 25(2), pp. 143-159 (2010).
Jacobsen et al., "Adjunctive 5-Hydroxytryptophan Slow-Release for Treatment-Resistant Depression: Clinical and Preclinical Rationale." Trends Pharmacol. Sci., vol. 37(11), pp. 933-944 (2016).
Jacobsen et al., "Deficient serotonin neurotransmission and depression-like serotonin biomarker alterations in tryptophan hydroxylase 2 (Tph2) loss-of-function mice." Molecular Psychiatry, vol. 17(7), pp. 694-704 (2012).
Jacobsen et al., "SSRI Augmentation by 5-Hydroxytryptophan Slow Release: Mouse Pharmacodynamic Proof of Concept." Neuropsychopharmacology. vol. 41(9), pp. 2324-2334 (2016).
Jacobsen et al., "The 5-HT deficiency theory of depression: perspectives from a naturalistic 5-HT deficiency model, the tryptophan hydroxylase 2Arg439His knockin mouse." Philos. Trans. R. Soc. Lond. B. Biol. Sci., vol. 367, pp. 2444-2456 (2012).
Jacobsen JPR, et al (2019). "Slow-release delivery enhances the pharmacological properties of oral 5-hydroxytryptophan: mouse proof-of-concept," Neuropsychopharmacology 44(12): pp. 2082-2090.
Kahn et al., "Effect of a serotonin precursor and uptake inhibitor in anxiety disorders: a double-blind comparison of 5-hydroxytryptophan, clomipramine and placebo." Int. Clin. Psychopharmacol., vol. 2(1), pp. 33-45 (1987).
Kahn RS, Westenberg HG (1985) "L-5-hydroxytryptophan in the treatment of anxiety disorders," J Affect Disord 8(2): 197-200.
Kapitany T, Schindl M, Schindler SD, Hesselmann B, Fureder T, Barnas C, et al (1999). The citalopram challenge test in patients with major depression and in healthy controls. Psychiatry Res 88(2): 75-88.
Kelwala S, et al. (1983) "History of antidepressants: successes and failures," The Journal of clinical psychiatry 44(5 Pt 2): 40-48.
Lader et al., "Efficacy and tolerability of escitalopram in 12- and 24-week treatment of social anxiety disorder: randomized, double-blind, placebo-controlled, fixed-dose study." Depress. Anxiety, vol. 19(4), pp. 241-248 (2004).
Levy A, Chen R (2016) "Myoclonus: Pathophysiology and Treatment Options," Curr Treat Options Neurol 18(5): 21.
Lopes et al., "Overview on gastroretentive drug delivery systems for improving drug bioavailability." Int. J. Pharm., vol. 510(1), pp. 144-158 (2016).
Lowe et al., "L-5-Hydroxytryptophan augments the neuroendocrine response to a SSRI." Psychoneuroendocrinology, vol. 31(4), pp. 473-484 (2006).
Magnussen et al., (1979) "Pharmacokinetics of Intravenously Administered L-5 Hydroxytryptophan in Man," Acta Parm. et toxicol. 44; pp. 308-314.
Magnussen I, et al. (1977) "Palatal myoclonus treated with 5-hydroxytryptophan and a decarboxylase-inhibitor," Acta Neurol Scand 55(3): 251-253.
Magnussen I, Mondrup K, Engbaek F, Lademann A, Olivarius BD (1982) "Treatment of myoclonic syndromes with paroxetine alone or combined with 5-HTP," Acta Neurol Scand 66(2): 276-282.
Manegold et al., "Aromatic L-amino acid decarboxylase deficiency: clinical features, drug therapy and follow-up." J. Inherit. Metab. Dis., vol. 32(3), pp. 371-380 (2009).
Mead et al., "Selective serotonin reuptake inhibitors for stroke recovery: a systematic review and meta-analysis." Stroke, vol. 44(3), pp. 844-850 (2013).
Meloni M, et al (2020b). "Efficacy and safety of 5-Hydroxytryptophan on levodopa-induced motor complications in Parkinson's disease: A preliminary finding," J Neurol Sci 415: 116869.
Meloni M, et al. (2020a). "Efficacy and safety of 5-hydroxytryptophan on depression and apathy in Parkinson's disease: a preliminary finding," Eur J Neurol 27(5): 779-786.
Meltzer H, et al. (1997) "Fluoxetine, but not tricyclic antidepressants, potentiates the 5-hydroxytryptophan-mediated increase in plasma cortisol and prolactin secretion in subjects with major depression or with obsessive compulsive disorder," Neuropsychopharmacology 17(1): pp. 1-11.
Meltzer HY, (1983) "Enhanced serum cortisol response to 5-hydroxytryptophan in depression and mania," Life Sci 33(25): 2541-2549.
Merck, Sinemet CR, Merck Sharp & Dohme Corp., 12 pages (2018).
Mitra et al., "Feasibility of mini-tablets as a flexible drug delivery tool." Int. J. Pharm., vol. 525(1), pp. 149-159 (2017).
Moore et al., (2005) "Portal 5-hydroxytryptophan infusion enhances glucose disposal in conscious dogs," american Jounral of Physlology-Endocrinology and Metabolism, vol. 289, 33 Pages.
Morrow et al., (2008) "Effects of Serotonergic Ativation by 5-Hydroxytryptophan on Sleep and Body Temperature of C57BL/6J and Interleukin-6-Deficient Mica are Dose and Time Related," Sleep, vol. 31, No. 1; pp. 21-33.
Murphy TK, et al. (2008) "SSRI adverse events: how to monitor and manage. International review od psychiatry," (Abingdon, England) 20(2): 203-208.
Nicolodi et al., "L-5-Hydroxytryptophan can prevent nociceptive disorders in man." Adv. Exp. Med. Biol., vol. 467, pp. 177-182 (1999).
Nokhodchi et al., "The role of oral controlled release matrix tablets in drug delivery systems." Bioimpacts, vol. 2(4), pp. 175-187 (2012).
Nord M, et al. (2013) "Effect of a single dose of escitalopram on serotonin concentration in the non-human and human primate brain," Int J Neuropsychopharmacol 16(7): pp. 1577-1586.
Notice of Publication corresponding to International Patent Application No. PCT/US2022/038914 dated Mar. 2, 2023.
Office Action (Final) corresponding to U.S. Appl. No. 17/525,961 dated Dec. 30, 2022.
Office Action (Restriction Requirement) corresponding to U.S. Appl. No. 17/252,961 dated Jan. 18, 2022.
Office Action corresponding to Israeli Patent Application No. 279509 dated Aug. 1, 2021.
Office Action corresponding to U.S. Appl. No. 17/252,961 dated Apr. 14, 2022.
Office Action corresponding to U.S. Appl. No. 17/877,699 dated Sep. 29, 2022.
Office Action corresponding to U.S. Appl. No. 17/877,699 dated Feb. 3, 2023.
Office Action corresponding to Vietnamese Application No. 1-2020-07497 dated Apr. 27, 2021.
Oquendo MA, et al (2014), "Toward a Biosignature for Suicide," Am J Psychiatry. 171(12); pp. 1-33.
Pahwa et al., "Randomized trial of IPX066, carbidopa/levodopa extended release, in early Parkinson's disease." Parkinsonism Relat. Disord., vol. 20(2), pp. 142-148 (2014).
Pereira VS, et al. (2018), "A brief history of antidepressant drug development: from tricyclics to beyond ketamine," Acta Neuropsychiatr 30(6): 307-322.
Perry et al., "Extracellular 5-hydroxytryptamine concentration in rat hypothalamus after administration of fluoxetine plus L-5-hydroxytryptophan." J. Pharm. Pharmacol., vol. 45(8), pp. 759-761 (1993).
Rao N (2007). "The clinical pharmacokinetics of escitalopram." Clin Pharmacokinet 46(4): pp. 281-290.
Rauws et al., "Comparative 90-day toxicity of two decarboxylase inhibitors, benserazide and carbidopa, in the rat." Toxicol. Appl. Pharmacol., vol. 66(2), pp. 201-220 (1982).
Rose et al., "The effect of carbidopa on plasma and muscle levels of L-dopa, dopamine, and their metabolites following L-dopa administration to rats." Mov. Disord., vol. 3(2), pp. 117-125 (1988).
Santucci M, et al. (1986) "L-5-hydroxytryptophan versus placebo in childhood migraine prophylaxis: a double-blind crossover study," Cephalalgia 6(3): 155-157.
Sargent et al., "Brain 5-HT neurotransmission during paroxetine treatment." Br. J. Psych., vol. 172, pp. 49-52 (1998).
Sharma et al., "To scale or not to scale: the principles of dose exploration." Br. J. Pharmacol., vol. 157(6), pp. 907-921 (2009).
Shenker Y, et al. (1985) "Central serotonergic stimulation of aldosterone secretion," J Clin Invest 76(4): pp. 1485-1490.

(56) References Cited

OTHER PUBLICATIONS

Shindo et al., "Mechanism of intestinal absorption and brain uptake of L-5-hydroxytryptophan in rats, as compared to those of L-3,4-dihydroxyphenylalanine." Chem. Pharm. Bull. (Tokyo), pp. 25(6), pp. 1417-1425 (1977).
Sloan et al., "Fluoxetine as a treatment for emotional lability after brain injury." Brain Inj., vol. 6(4), pp. 315-319 (1992).
Smarius LJ, et al (2008) "Pharmacology of rising oral doses of 5-hydroxytryptophan with carbidopa," J Clin Psychopharmacol 22(4): 426-433.
Smith BP, et al (2000). "Confidence interval criteria for assessment of dose proportionality," Pharm Res 17(10): pp. 1278-1283.
Soulairac et al., "Effect of 5-hydroxytryptophan, a serotonin precursor, on sleep disorders." Ann. Med. Pyschol. (Paris), vol. 1(5), pp. 792-798 (1977).
Steiner et al., "Fluoxetine in the treatment of premenstrual dysphoria. Canadian Fluoxetine/Premenstrual Dysphoria Collaborative Study Group." N. Engl. J. Med., vol. 332(32), pp. 1529-1534 (1995).
Sutton, "The use of gastrointestinal intubation studies for controlled release development." Br. J. Clin. Pharmacol. vol. 68(3), pp. 342-354 (2009).
Takahashi et al., "Measurement of 5-hydroxyindole compounds during L-5-HTP treatment in depressed patients." Folia. Psychiatr. Neurol. Jpn., vol. 30(4), pp. 463-473 (1976).
Tang SJ, (2002) "The novel use of an intravenous proton pump inhibitor in a patient with short bowel syndrome," J Clin Gastroenterol 34(1): 62-63.
Taylor MJ, et al. (2006) "Early onset of selective serotonin reuptake inhibitor antidepressant action: systematic review and meta-analysis," Arch Gen Psychiatry 63(11): pp. 1-15 Pages.
Thombre AG (2005). Assessment of the feasibility of oral controlled release in an exploratory development setting. Drug Discov Today 10(17): 1159-1166.
Thombre et al., "Osmotic drug delivery using swellable-core technology." J. Control Release, vol. 94(1), pp. 75-89 (2004).
Timmermans et al., "Factors controlling the buoyancy and gastric retention capabilities of floating matrix capsules: New data for reconsidering the controversy." J. Pharm. Sci., vol. 83, pp. 18-24 (1994).
Trivedi MH, et al (2006) "Evaluation of outcomes with citalopram for depression using measurement-based care in STAR*D: implications for clinical practice," The American journal of psychiatry 163(1): pp. 28-40.
Trouillas et al., "Improvement of cerebellar ataxia with levorotatory form of 5-hydroxytryptophan. A double-blind study with quantified data processing." Arch. Neurol., vol. 45(11), pp. 1217-1222 (1988).
Turner et al., "Serotonin a la carte: supplementation with the serotonin precursor 5-hydroxytryptophan." Pharmacol. Ther., vol. 109(3), pp. 325-338 (2006).
Van Hiele, L-5-Hydroxytryptophan in depression: the first substitution therapy in psychiatry? The treatment of 99 out-patients with "therapy resistant" depressions. Neuropsychobiology, vol. 6(4), pp. 230-240 (1980).
Van Praag, "Serotonin precursors in the treatment of depression." Adv. Biochem. Psychopharmacol., vol. 34, pp. 259-286 (1982).

Van Vliet et al. (1996) "Behavioral, neuroendocrine and biochemical effects of different doses of 5-HTP in panic disorder," European neuropsychopharmacology : the journal of the European College of Neuropsychopharmacology 6(2): 103-110.
Van Woert et al., "Long-term therapy of myoclonus and other neurologic disorders with L-5-hydroxytryptophan and carbidopa." N. Engl. J. Med., vol. 296(2), pp. 70-75 (1977).
Veenstra-VanderWeele et al., "Autism gene variant causes hyperserotonemia, serotonin receptor hypersensitivity, social impairment and repetitive behavior." Proc. Natl. Acad. Sci. USA, vol. 109(14), pp. 5469-5474 (2012).
Verhagen Metman et al., "Gastroretentive carbidopa/levodopa, DM-1992, for the treatment of advanced Parkinson's disease." Mov. Disord., vol. 30(9), pp. 1222-1228 (2015).
Vigliante I, et al. (2019). "Chemical Characterization and DNA Fingerprinting of Griffonia simplicifolia Baill," Molecules 24(6);pp. 1-9.
Viscogliosi et al., "Efficacy and Safety of Citalopram Compared to Atypical Antipsychotics on Agitation in Nursing Home Residents With Alzheimer Dementia." J. Am. Med. Dir. Assoc., vol. 18(9), pp. 799-802 (2017).
Westenberg et al., "Kinetics of L-5-hydroxytryptophan in healthy subjects." Psychiatry Res., vol. 7(3), pp. 373-385 (1982).
Yeh et al., "Pharmacokinetics and bioavailability of Sinemet CR: A summary of human studies," Neurology, vol. 39(Suppl. 2), pp. 25-38 (1989).
Yoshimura et al., "Involvement of dopamine in development of hypertension in spontaneously hypertensive rat: effect of carbidopa, inhibitor of peripheral dopa decarboxylase." Clin. Exp. Hypertens. A., vol. 9(10), pp. 1585-1599 (1987).
Yousefzadeh F, et al (2020), "5-Hydroxytryptophan as adjuvant therapy in treatment of moderate to severe obsessive-compulsive disorder: a double-blind randomized trial with placebo control," elnt Clin Psychopharmacol.
Zalsman G, et al (2016). "Suicide prevention strategies revisited: 10-year systematic review," Lancet Psychiatry 3(7): 646-659.
Chen C. et al., (2012), "Pharmacokinetics and pharmacodynamics of gastroretentive delivery of levodopa/cardibopa in patients with Parkinson disease," Clinical neuropharmacology 35 (2): 67-72.
Hou et al (2003) "Gastric retentive dosage forms: a review," Crit. Rev Ther Drug Carrier Syst 20(6): 459-497.
Maurer (2016), "Gastrointestinal Motility, Part 2: Small-Bowel and Colon Transit," J. Nucl. Med 56 (9): 1395-1400.
Notice of Publication of U.S. Appl. No. 17/877,699 dated Feb. 17, 2023.
Notice of Allowance and Fees Due corresponding to U.S. Appl. No. 17/877,699 dated Apr. 20, 2023.
Othman, et al (2015), "Jenjunal Infusion of levodopa-carbidopa intestinal gel versus oral administration of levodopa-carbidopa tablets in Japanese subjects with advanced Parkinson's disease: pharmacokinetics and pilot efficacy and safety," Clinical pharmacokinetics 54 (9): 975-984.
Ramaekers et al, (2001) "A novel neurodevelopmental syndrome responsive to 5-hydroxytryptophan and carbidopa," Molecular genetics and metabolism 73(2): 179-187.

\* cited by examiner

METHOD FOR OPTIMIZING 5-HYDROXYTRYPTAMINE FUNCTION IN THE BRAIN FOR THERAPEUTIC PURPOSES

CROSS REFERENCE TO RELATED APPLICATIONS

This application claims priority to and the benefit of U.S. Provisional Patent Application Ser. No. 63/255,647, filed Oct. 14, 2021, the disclosure of which is incorporated herein by reference in its entirety.

TECHNICAL FIELD

The presently disclosed subject matter relates to methods and compositions for treating disorders of the brain using intravenous 5-hydroxytryptophan (5-HTP).

BACKGROUND

The listing or discussion of an apparently prior-published document in this specification should not necessarily be taken as an acknowledgement that the document is part of the state of the art or is common general knowledge.

Mood disorders, anxiety disorders, obsessive compulsive disorder, impulse control disorders, and suicidal ideation represent large unmet healthcare needs. The pathogenesis of these disorders can, at least in part, involve deficiencies in brain 5-hydroxytryptamine (5-HT) function. Conversely, modulating the brain 5-HT system is one therapeutic avenue in treating such disorders.

The functionally active pool of brain 5-HT is the extracellular 5-HT (5-HT$_{Ext}$). 5-HT$_{Ext}$ is the 5-HT released from the neuron and acting on 5-HT receptors, which in turn elicits down-stream neurobiological events. Various drugs that increase brain levels of 5-HT$_{Ext}$ have been reported to treat the above-mentioned disorders, as well as other disorders. However, currently available 5-HT$_{Ext}$-elevating drugs have limitations. For example, therapeutic onset of currently available 5-HT$_{Ext}$-elevating drugs typically does not occur until at least one week into treatment, with full efficacy typically taking six weeks (Taylor et al, 2006). In addition, efficacy is most often partial. Many patients experience no therapeutic benefit from currently available 5-HT$_{Ext}$-elevating drugs (Trivedi et al, 2006).

Current 5-HT$_{Ext}$-elevating drugs generally work by inhibiting a single biological negative regulator of 5-HT$_{Ext}$. For instance, serotonin reuptake inhibitors block the serotonin transporter, the membrane transporter that transports 5-HT released extracellularly back into the neuron (Jacobsen et al, 2016b). Monoamine oxidase inhibitors block the main metabolic pathway for 5-HT (Kelwala et al, 1983). No current 5-HT$_{Ext}$-elevating drug approved by the US Food and Drug Administration (FDA) works via strengthening the brain's endogenous 5-HT system, e.g., by making more 5-HT available, while leaving dynamic 5-HT regulatory mechanisms intact.

Despite decades of intense and costly research by academia and pharma, no substantial improvement in efficacy and onset of therapeutic action of 5-HT$_{Ext}$-elevating psychiatric drugs has been seen since the 1960s (Pereira and Hiroaki-Sato, 2018).

Accordingly, there is an ongoing need for additional methods for increasing brain 5-HT$_{Ext}$ levels and for treating neurological and psychiatric disorders associated with deficiencies in brain 5-HT$_{Ext}$. In particular, there is an ongoing need for methods and compositions for increasing brain 5-HT$_{Ext}$ quickly and/or with a low incidence of severe or moderate adverse effects.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned, likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a method of elevating brain extracellular 5-hydroxytryptamine (5-HT$_{Ext}$) in a subject in need thereof, wherein the method comprises administering 5-hydroxytryptophan (5-HTP) to the subject as a continuous intravenous (IV) infusion over an infusion treatment period lasting about four hours or more at an 5-HTP infusion rate of about 0.01 milligrams per kilogram body weight per hour (mg/kg/hr) to about 0.125 mg/kg/hr on average over the infusion treatment period, wherein the administering provides a 5-HTP plasma exposure, as an area under plasma concentration versus time curve extrapolated to infinity (AUC$_{inf}$, in hours times nanograms per milliliter (ng/ml)), of about 3500 times total dose of 5-HTP (in mg/kg) administered over the infusion treatment period.

In some embodiments, the 5-HTP infusion rate is constant throughout the infusion treatment period. In some embodiments, the 5-HTP infusion rate is about 0.0417 mg/kg/hr and the administering provides a steady state 5-HTP plasma level of about 100 ng/ml. In some embodiments, the 5-HTP infusion rate is about 0.0833 mg/kg/hr and the administering provides a steady state 5-HTP plasma level of about 200 ng/ml. In some embodiments, the 5-HTP infusion rate is about 0.125 mg/kg/hr and the administering provides a steady state 5-HTP plasma level of about 300 ng/ml.

In some embodiments, the 5-HTP infusion rate is variable over the infusion treatment period. In some embodiments, the continuous IV infusion is performed at a first 5-HTP infusion rate for a first portion of the infusion treatment period and at a second 5-HTP infusion rate for a second portion of the infusion treatment period, wherein the first 5-HTP infusion rate is lower than the second 5-HTP infusion rate.

In some embodiments, the infusion treatment period is about 4 hours to about 24 hours. In some embodiments, the infusion treatment period is about 24 hours and the total dose of 5-HTP administered is about 1 mg/kg to about 3 mg/kg. In some embodiments, the infusion treatment period is longer than 24 hours.

In some embodiments, the method further comprises administering to the subject a 5-HT$_{Ext}$-elevating compound. In some embodiments, the 5-HT$_{Ext}$-elevating compound is a serotonin reuptake inhibitor and the subject is being simultaneously treated with the serotonin reuptake inhibitor and/or has been pre-treated with the serotonin reuptake inhibitor.

In some embodiments, the administering provides an increase in plasma cortisol concentration in the subject compared to a subject not treated with the continuous IV infusion of 5-HTP. In some embodiments, the method is free of severe and moderate adverse effects associated with administration of the continuous IV infusion of 5-HTP. In some embodiments, the method is free of administering a peripheral decarboxylase inhibitor to the subject. In some embodiments, the method further comprises administering to the subject an anti-emetic. In some embodiments, the anti-emetic is a 5-HT$_3$ receptor antagonist.

In some embodiments, the subject is a human in need of treatment for a neurological or psychiatric disorder. In some embodiments, the neurological or psychiatric disorder is suicidal ideation or acute worsening of a mood disorder.

In some embodiments, the method further comprises administering an additional treatment to the subject after completion of the infusion treatment period to maintain the therapeutic effect. In some embodiments, the additional treatment comprises administration of a slow-release formulation including 5-HTP. In some embodiments, administration of the additional treatment is initiated within about 24 hours of the completion of the infusion treatment period.

In some embodiments, the presently disclosed subject matter provides a stable pharmaceutical solution for use in preparing an infusate fluid for continuous intravenous (IV) infusion for elevating brain extracellular 5-hydroxytryptamine (5-HT$_{Ext}$) in a mammal, wherein said solution comprises 5-hydroxytryptophan (5-HTP) and water and is stable for at least 12 months stored at 5° C. under an inert gas or nitrogen in the dark. In some embodiments, the solution has a 5-HTP concentration of about 5 milligrams per milliliter.

Accordingly, it is an object of the presently disclosed subject matter to provide methods of elevating brain 5-HT$_{Ext}$ via continuous IV infusion of 5-HTP and compositions for treating suicidal ideation or acute worsening of mood disorders via continuous IV infusion of 5-HTP. An object of the presently disclosed subject matter having been stated hereinabove, and which is achieved in whole or in part by the presently disclosed subject matter, other objects will become evident as the description proceeds when taken in connection with the accompanying drawings and examples as best described herein below.

BRIEF DESCRIPTION OF THE DRAWINGS

In order that the disclosure may be readily understood and put into practical effect, reference will now be made to examples as illustrated with reference to the accompanying figures. The figures together with the description serve to further illustrate the embodiments of the presently disclosed subject matter and explain various principles and advantages.

DETAILED DESCRIPTION

Figure 1:
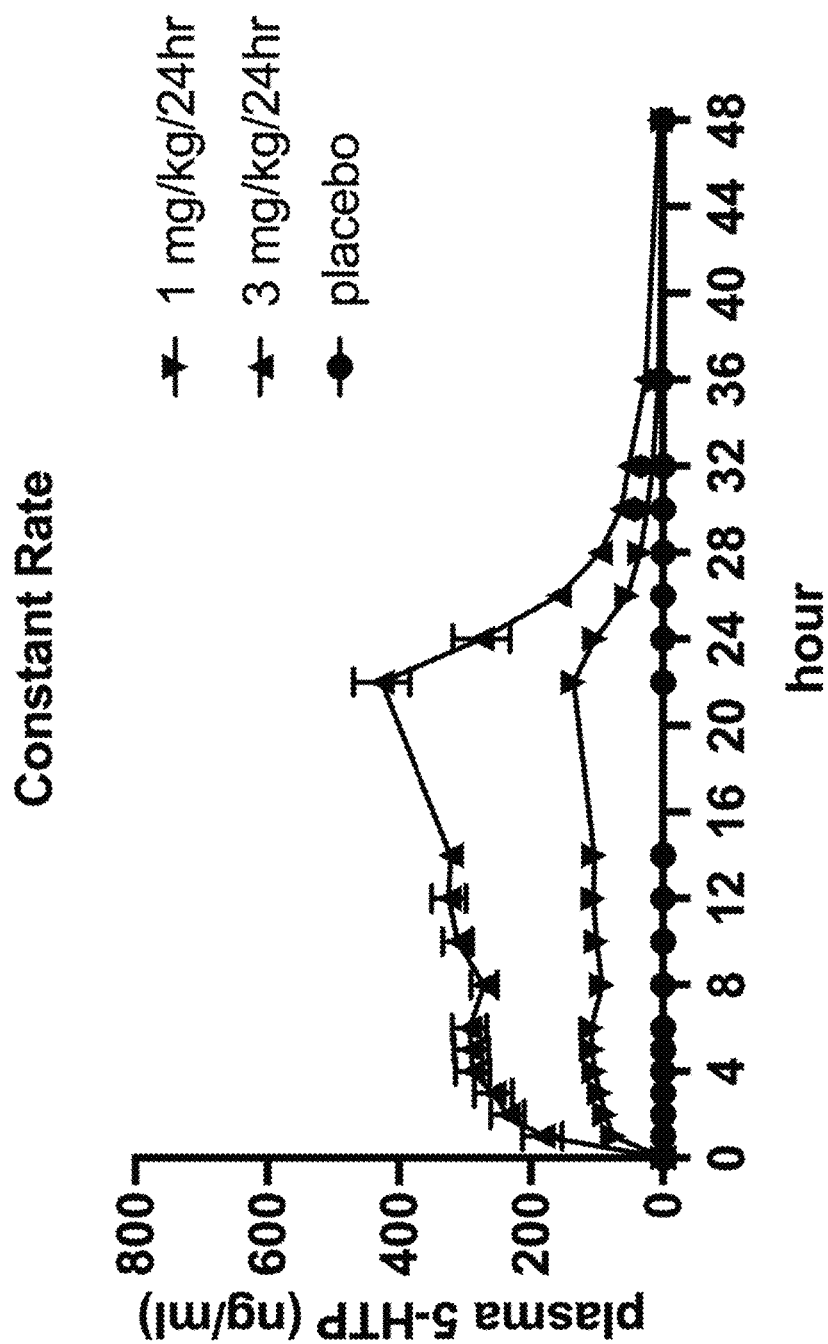
FIG. 1 is a graph showing plasma 5-hydroxytryptophan (5-HTP) concentration (nanograms per milliliter (ng/ml)) versus time profiles of ascending constant 5-HTP infusion rates for continuous intravenous (IV) infusion using a constant flow rate for 24 hours. Data for a constant 5-HTP infusion rate of 1 milligram per kilogram per day (mg/kg/24 hr), i.e., "1 mg/kg/24 hr" is shown in downward-pointing triangles, while that for a constant 5-HTP infusion rate of 3 mg/kg/24 hr, i.e., "3 mg/kg/24 hr" is shown in upward-pointing triangles. Data for a placebo is shown in circles. Data shown are means t standard error of mean (SEM).

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "an agent" or "a polymer" includes a plurality of such agents or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

In pharmacokinetics and as used herein, "steady state" refers to the situation where the overall intake of an active pharmaceutical compound is fairly in dynamic equilibrium with its elimination. Thus, the average plasma level of the compound remains the same from day to day, although there can be intra-day fluctuations related to dosing.

The term "pharmaceutically acceptable" means approved by a regulatory agency of the Federal or a state government or listed in the U.S. Pharmacopeia or other generally recognized pharmacopeia for use in animals, and more particularly in humans.

The term "continuous intravenous (IV) infusion" refers to delivery of a dose of a therapeutic agent via IV administration to a subject over a prolonged and sustained period of time, such as about two hours or more (e.g., about 4 hours or more). Continuous IV infusion as used herein contrasts with bolus IV infusion or injection, which typically involves administration of a single, discrete dose of a therapeutic agent over a short time period (typically less than about 60 minutes) or the administration of a multiple discrete bolus doses separated by periods of time where no therapeutic agent is being administered.

The term "neurological disorder" as used herein refers diseases and disorders that affect the brain, spinal cord, and nerves, such as, but not limited to, epilepsy and other seizures, migraines, headaches, learning disorders, multiple sclerosis, cerebral palsy, autism, Alzheimer's disease, Parkinson's disease, agitation related to neurological disorders (e.g., Alzheimer's disease or Parkinson's disease) amyotrophic lateral sclerosis (ALS), ataxia, phenylketonuria, fibromyalgia, myoclonus, head injuries, brain tumors, and stroke.

The term "psychiatric disorder" refers to a variety of mental, emotional and behavior disorders, including but not limited to, depressive disorders (including major depression, dysthymia (e.g., premenstrual dysthymia), post-partum depression, depression related to another health condition (e.g., cancer, infection, or injury), substance-induced depression (e.g., depression related to medication use (such as depression related to interferon use), depression related to drug use, depression related to alcohol use, or depression related to toxin exposure) and other mood disorders (e.g., bipolar disorder), attention deficit hyperactivity disorder (ADHD), schizophrenia, suicidal ideation, anxiety disorders (e.g., obsessive-compulsive disorder (OCD), social anxiety, panic disorder, generalized anxiety, or post-traumatic stress disorder (PTSD)), personality disorders (e.g., borderline personality disorder), eating disorders (e.g., anorexia or bulimia), psychotic disorders, substance abuse disorders, and dementia.

The term "mood disorder" refers to a subset of psychiatric disorders including but not limited to major depression, dysthymia, bipolar disorder, depression related to another health condition, and substance-induced depression.

"Acute worsening of a mood disorder" as used herein refers to a worsening of a subject's symptoms of a mood disorder that would, in the opinion of a medical practitioner, suggest that the subject would benefit from or is in need of urgent medical intervention, e.g., a change in therapeutic approach (e.g., a change from one type of therapeutic agent to another type of therapeutic agent), the addition of an additional therapeutic approach, an increase in dose of a therapeutic agent, or hospitalization.

The terms "depressive disorder" or "depression" refer to a mood disorder in which feelings of sadness, loss of interest in things that previously gave pleasure, anger, or frustration interfere with everyday life for a significant period of time. Depression can be caused by biochemical imbalances in the brain, hereditary factors, adverse life events, organic disease, and a combination of factors. Symptoms of depression can include one or more of: agitation, restlessness, and irritability; a significant change in appetite, often with weight gain or loss; difficulty concentrating; fatigue and lack of energy; feelings of hopelessness and helplessness, or feelings or anger or discouragement; feelings of worthlessness, self-hate, and inappropriate guilt; inactivity and withdrawal from usual activities, a loss of interest or pleasure in activities that were once enjoyed; thoughts of death or suicide; trouble sleeping or excessive sleeping.

"Major depressive disorder" or "major depression" (also called "unipolar depression" or "unipolar major depression") as used herein has its usual meaning in the art, and is typically characterized by the presence of at least five of the depression symptoms noted above for at least two weeks.

Criteria for major depression are specified in the Diagnostic and Statistical Manual of Mental Disorders, 5th Edition: DSM 5).

"Anxiety disorder" or "anxiety" as used herein refer to abnormal or pathological fear or phobia and can be continuous or episodic. Symptoms of anxiety can include one or more of: mental apprehension, physical tension, and physical symptoms such as panic attacks or symptoms associated with hyperventilation. Anxiety disorders include generalized anxiety disorder, social anxiety, panic disorder, OCD, and PTSD.

"Suicidal ideation" refers to thinking about or having an intention of taking one's life. "Suicidal ideation" can refer to thoughts about or an unusual preoccupation with suicide, or thoughts of ending one's life or not wanting to live anymore whether or not any active efforts are made to do so. The range of suicidal ideation varies from fleeting to chronic and can progress to detailed planning, role playing, and unsuccessful attempts, which can, in some embodiments, be deliberately constructed to fail or be discovered, or, can be fully intended to result in death. Factors which can be considered in making a diagnosis include one or more of: the patient's history, including a history of previous attempts or a family history of suicide; answers during clinical interview in which the subject is asked whether they are presently thinking of suicide, whether they have made actual plans to do so, whether they have thought about the means, and/or what they think their suicide will accomplish; a suicide note, if any; information from friends or relatives; outcomes of psychiatric tests, such as, but not limited to, the Beck Depression Inventory (BDI), the Depression Screening Questionnaire. and the Hamilton Depression Rating Scale; and the patient's mood, appearance, vocal tone, and similar factors. Additional tools for evaluation of suicidal ideation include the Beck Scale for Suicide Ideation (BSS), the Columbia Suicide Severity Rating Scale (C-SSRS), Suicidal Ideation and Behavioral Assessment Tool (SIBAT), the Clinical Global Impression-Severity of Suicidality-Revised (CGI-SS-R), the Mini-International Neuropsychiatric Interview (MINI), and the Frequency of Suicidal Thinking (FoST).

Suicidal ideation can be acute or chronic. The term "acute suicidal ideation" as used herein refers to a subject having an onset or increase in symptoms (i.e., thoughts about death, planning and/or actions) within the last about 7 days. As used herein "acute suicidal ideation" can also refer to a patient with high levels of suicidal ideation, including, in some embodiments, intent to act on their suicidal ideation and current suicidal capabilities to do harm to themselves in the immediate future. Immediate future is a short-defined period of time usually less about 1 week, less than 2 days, less than 1 day or less than a few hours. In contrast, a subject with chronic suicidal ideation is a subject with on-going symptoms (e.g., lasting more than one week, one month, one year or more).

"Obsessive compulsive disorder" (or OCD) refers to a type of anxiety disorder primarily characterized by repetitive obsessions (distressing, persistent, and intrusive thoughts or images) and/or compulsions (urges to perform specific acts or rituals). Often the process is entirely illogical and/or inexplicable. For example, a compulsion of walking in a certain pattern can be used to alleviate an obsession of impending harm.

"Attention deficit hyperactivity disorder" refers to an abnormal problem (considering the normal range based on a subject's age and development) with inattentiveness, overactivity, and/or impulsivity. Though the cause of ADHD is unknown, imaging studies of the brains of children with ADHD suggest that there may be an imbalance of neurotransmitters (e.g., dopamine, serotonin, and adrenaline) associated with the disorder.

"Substance abuse" as used herein has its usual meaning and includes both alcohol abuse or addiction (e.g., alcoholism, or alcoholic subjects), as well as abuse or addiction to drugs such as narcotics, opiates, stimulants, depressants, etc. (e.g., barbiturates, ecstasy, cocaine, crack cocaine, morphine, heroin, amphetamine, methamphetamine, oxycontin, etc.).

The term "adverse event" (or AE) as used herein has its usual meaning and refers to undesirable medical outcomes (e.g., undesirable symptoms) in a subject being treated (e.g., being administered a pharmaceutical composition). The adverse event has a temporal relationship with the treatment but can or cannot have a causal relationship with the treatment. Adverse events that can be associated with 5-HTP include, but are not limited to, diarrhea, upset stomach, nausea, vomiting and serotonin toxicity.

A "mild adverse event" as used herein refers to an adverse event that involves a symptom or symptoms that cause low level discomfort and/or that are transient. Mild adverse events generally do not interfere with normal daily activities or result in a need for medical intervention.

A "moderate adverse event" as used herein refers to an adverse event involving symptoms significant enough to interfere with or limit daily activities and can, in some embodiments, lead to the use of a medical intervention to resolve or lessen the symptoms related to the adverse event.

A "severe adverse event" as used herein refers to an adverse event that involves symptoms significant enough to prevent normal activities. Severe adverse events can result in the use of medical intervention (e.g., hospitalization).

The term "5-HTP infusion rate" as used herein refers to an amount of 5-HTP (generally in milligrams per kilogram subject body weight (mg/kg)) administered via infusion per unit time (e.g., per hour (hr or h) or per day (e.g., 24 hr). In some embodiments, the 5-HTP infusion rates described herein are average 5-HTP infusion rates over an entire infusion treatment period. In some embodiments, the 5-HTP infusion rate is constant over the entire infusion period, i.e., is a constant 5-HTP infusion rate. Thus, in some embodiments, a given average 5-HTP infusion rate is the same as the constant 5-HTP infusion rate. In some embodiments, the 5-HTP infusion rate is not constant over the entire infusion period. Thus, in some embodiments, the 5-HTP infusion is performed using a series of transient sub-infusion rates that are different from one another (i.e., are variable) and that together, over the course of the entire infusion treatment period, provide a given average 5-HTP infusion rate for the infusion treatment period. Thus, when the 5-HTP infusion rate is variable over the infusion treatment period, the particular transient 5-HTP infusion rate (e.g., a "first infusion rate for a first portion of the infusion treatment period") in any given portion of time in the total infusion treatment period can be higher or lower than the 5-HTP infusion rate provided as the average 5-HTP infusion rate for the infusion treatment period as a whole. However, according to the presently disclosed subject matter the transient 5-HTP infusion rates are greater than 0 mg/kg/hr or 0 mg/kg/24 hr. In some embodiments, average 5-HTP infusion rates in infusion methods with varied 5-HTP infusion rates over the infusion treatment period are referred to as "ramp rates."

The term "total dose" as used herein refers to the total amount of 5-HTP (e.g., typically expressed in milligrams per kilogram subject body weight (mg/kg)) administered during the entire course of an infusion treatment period of a continuous IV infusion treatment method of the presently disclosed subject matter. For example, a total dose of a 5-HTP at a 5-HTP infusion rate (i.e., an average 5-HTP infusion rate) of 0.125 mg/kg/hr or 3 mg/kg/24 hr for an infusion treatment period of 12 hours is 1.5 mg/kg.

II. General Considerations

Suicide and suicidal ideation represent a significant unmet need. In the United States of America, the suicide rate has risen 35% since year 2000 (American Foundation for Suicide Prevention). The pathogenesis of suicide is believed to involve genetic, environmental, and neurobiological factors, the latter prominently including 5-HT brain deficiency (Oquendo et al, 2014). There are no FDA-approved drugs for suicidal ideation treatment or suicide prevention in general. Clozapine is FDA-approved for protecting against suicide in the context of schizophrenia (Zalsman et al, 2016). Lithium is generally accepted to protect against suicide in bipolar disorder (Zalsman et al, 2016). Ketamine-derived drugs has been proposed for treatment of acute suicidality in mood disorders, although large randomized controlled trials found no effects (Fu et al, 2020). Clozapine, lithium, and ketamine work primarily via therapeutic mechanisms distinct from elevating brain 5-HT$_{Ext}$ (Zalsman et al, 2016).

Selective serotonin reuptake inhibitors (SSRIs) make up a main class of 5-HT$_{Ext}$-elevating drugs. SSRIs are FDA-approved for treating depression, anxiety, OCD, and post-traumatic stress disorder (PTSD). SSRIs can be modestly protective against future suicide attempts, but only after many weeks of treatment, and only in adult patients (Gibbons et al, 2012). Further, in the short-term, SSRIs can increase suicidal ideation and behaviors, particularly in young people, and therefore carry black-box warnings from the FDA and the European Medicines Agency (Murphy et al. 2008). Thus, to date, available clinical data suggests against the likelihood that a 5-HT$_{Ext}$-elevating drug could treat suicidality with a fast onset, i.e., within hours or days.

Recent brain imaging studies indicate that SSRIs paradoxically can acutely, temporarily decrease brain 5-HT$_{Ext}$ in humans (Nord et al, 2013), while long-term SSRI treatment only elevates 5-HT$_{Ext}$ modestly and inconsistently (Haahr et al, 2014). While it is not desired to be bound by a particular theory of operation, such findings could be wholly or partially explanatory for why SSRIs and similar drugs exacerbate apparent suicide risk in the short term and only having modest and inconsistent efficacy across their indications in the long term.

In the body, 5-HT is synthesized from dietary tryptophan via an intermediate precursor, 5-hydroxytryptophan (5-HTP). Only a few percent of dietary tryptophan are converted to 5-HTP. The tryptophan to 5-HTP conversion is the rate-limiting step in 5-HT synthesis, catalyzed by the enzyme tryptophan hydroxylase (Jacobsen et al, 2016b). 5-HTP is in turn converted to 5-HT, catalyzed by aromatic amino acid decarboxylase, an enzyme present in the intestine, many peripheral tissues, and in the brain (Bowsher R. R., 1986).

There are no FDA- or EMA-approved 5-HTP drug products currently on the market. But exogenously administered 5-HTP has been used experimentally since the 1960s as a therapeutic, mainly as an antidepressant (Turner et al, 2006), but also, for example, for anxiety, myoclonus, ataxia, fibromyalgia, pain, obesity, and OCD (Birdsall, 1998; Levy and Chen, 2016; Yousefzadeh et al, 2020). Most prior studies using 5-HTP experimentally to treat a human disorder concerned chronic (e.g., weeks, months, years) oral treatment. Often, a peripheral decarboxylase inhibitor (PDI) is co-administered to enhance the pharmacokinetics of the 5-HTP via decreasing peripheral conversion of 5-HTP to 5-HT (Jacobsen et al, 2016b). The therapeutic onset of oral 5-HTP is delayed, with clinically meaningful therapeutic effects occurring only after at least 1 week of treatment, and usually later (van Hiele, 1980).

5-HTP in its native immediate release form is known to cause bothersome adverse events. After oral treatment, 5-HTP is well-known to cause rapid gastrointestinal adverse events, such as diarrhea and upset stomach, stemming from extensive conversion of 5-HTP to 5-HT in the gastrointestinal tract (Turner et al, 2006). Further, 5-HTP not converted to 5-HT in the intestinal tissue is rapidly transported into the blood stream, causing a spike in brain 5-HTP and hence brain 5-HT, which frequently causes nausea and vomiting (Lowe et al, 2006; Smarius et al, 2008). Such drug spiking above the therapeutic window—so-called $C_{Max}$-effects (Thombre, 2005)—appears important for causing the adverse events arising from native 5-HTP (Jacobsen et al, 2016b).

III. Representative Embodiments

In some embodiments, the presently disclosed subject matter provides a method to rapidly and reliably elevate brain 5-HT$_{Ext}$ in an individual in need thereof over a prolonged period of time, i.e., over a few hours or one or several days. Elevated brain 5-HT$_{Ext}$ leads to increased 5-HT neurotransmission, 5-HT receptor stimulation, and downstream biological events, e.g., associated with enhanced mood, enhanced sociability, increased cognitive and behavioral flexibility, decreased aggression and/or decreased impulsivity.

In some embodiments, the method of providing elevated brain 5-HT$_{Ext}$ according to the presently disclosed subject matter is a continuous IV infusion of 5-HTP. A continuous IV 5-HTP infusion can provide elevation of brain 5-HT$_{Ext}$ in a substantially more controlled fashion than oral administration of 5-HTP, as (i) the dose can be individualized on a mg per kg basis and (ii) the IV route avoids the inherent variability with drug absorption from the gastrointestinal tract. Simultaneously, continuous IV 5-HTP infusion combines the ability to rapidly achieve therapeutic 5-HTP levels while avoiding/minimizing the 5-HTP/5-HT $C_{Max}$ spikes associated with bothersome adverse events. In some embodiments, the method comprises administering a total dose of 5-HTP to the subject as a continuous IV infusion over an infusion treatment period (or "IV 5-HTP infusion treatment period") lasting about four hours or more, wherein the administering provides a 5-HTP plasma exposure, as an area under plasma concentration versus time curve extrapolated to infinity (AUC$_{Inf}$, in hours times nanograms per milliliter (ng/ml)), of about 3500 times the total dose of 5-HTP (in milligrams (mg) 5-HTP per kilogram (kg) body weight).

Accordingly, in some embodiments, the presently disclosed subject matter provides a method of treating a neurological or psychiatric disorder in a subject in need of treatment thereof, wherein the method comprises administering to the subject a therapeutically effective amount of 5-HTP via IV infusion (i.e., continuous IV infusion). Thus, in some embodiments, the 5-HTP is provided in an infusate fluid that is administered intravenously to the subject for a continuous and sustained period of time (e.g., at least four hours or more). In some embodiments, the method comprises administering 5-HTP to the subject as a continuous IV infusion over an infusion treatment period lasting about four hours or more at a 5-HTP infusion rate of about 0.01 milligrams per kilogram body weight per hour (mg/kg/hr) to about 0.125 mg/kg/hr on average over the infusion treatment period, wherein the administering provides a 5-HTP plasma exposure, as an $AUC_{Inf}$ (in hours times ng/ml), of about 3500 times the total dose of 5-HTP (i.e., the total amount of 5-HTP administered via IV infusion over the course of the infusion treatment period in mg 5-HTP per kg body weight). In some embodiments, the IV 5-HTP infusion is delivered over an infusion treatment period of about 4 hours to about 144 hours (e.g., about 4, 8, 12, 16, 20, 24, 28, 32, 36, 40, 44, 48, 52, 56, 60, 64, 68, 72, 76, 80, 84, 88, 92, 96, 100, 104, 108, 112, 116, 120, 124, 128, 132, 136, 140 or 144 hours). In some embodiments, the infusion treatment period is about 12 hours to about 24 hours.

In some embodiments, the continuous IV 5-HTP infusion is performed at a constant infusion rate (i.e., so that the amount of 5-HTP administered per unit time is constant over the entire course of the infusion treatment period). In some embodiments, essential steady-state 5-HTP plasma levels, i.e., about 80% of average plasma levels after levels cease to increase, can be achieved by the presently disclosed methods in about 4 hours to about 6 hours, e.g., when the 5-HTP infusion rate is constant. In some embodiments, the essential steady-state 5-HTP plasma level is achieved in about 4 hours, in about 4.5 hours, in about 5 hours, in about 5.5. hours or in about 6 hours. However, variable 5-HTP infusion rates (e.g., involving variable infusion volume rates when using a single infusate fluid of a given 5-HTP concentration or involving sequential use of multiple infusate solutions that differ in 5-HTP concentration) can also be used. In some embodiments, the initial infusion rate is higher, to achieve therapeutic 5-HTP plasma levels faster, followed by a lower maintenance infusion rate. In some embodiments, the initial 5-HTP infusion rate is lower, to optimize tolerability when needed, followed by 1 or more ramp-up steps in the infusion rate to achieve the maintenance infusion rate. In yet other embodiments, the infusion is terminated gradually, by 1 or more gradual ramp-downs in the infusion rate. If only a partial therapeutic response is achieved, and tolerability is acceptable, the infusion volume rate can be increased, or the concentration of 5-HTP in the infusate fluid can be increased, to raise the steady-state 5-HTP plasma levels.

Representative advantages of continuous IV infusion vs oral delivery of 5-HTP include but are not limited to the following: (a) more uniform and predictable 5-HTP plasma levels; (b) higher 5-HTP plasma levels (e.g., as gastrointestinal adverse events can be reduced and 1st pass metabolism (e.g., over the gastrointestinal wall) can be reduced); and (c) ability to rapidly reduce the dose by reducing infusion flow-rate (i.e., infusion volume rate) or reducing the 5-HTP concentration in the infusate fluid or to terminate the treatment by stopping the infusion if adverse events occur, equaling enhanced safety.

By way of example and not limitation, the 5-HTP for IV solutions (i.e., infusate fluids) can be extracted from the seeds of *Griffonia simplicifolia* (Vigliante et al, 2019). In some embodiments, the 5-HTP has a purity of 95%, 98%, 99%, or above 99.5%. In some embodiments, the 5-HTP is the L-enantiomer, the naturally occurring enantiomer. Alternatively, the 5-HTP is a mixture of the L- and D-enantiomers. Unless otherwise mentioned herein, the weight of 5-HTP is the weight of the free base of 5-HTP. Any salts or solvates that may be used will accordingly have a higher mass value.

In some embodiments, a PDI is co-administered with the 5-HTP, either in the same solution (i.e., the same infusate fluid), in a different solution, or in a different dosage form, for which non-exhaustive examples include a tablet, capsule, or patch. A PDI can, in a dose-dependent fashion, elevate 5-HTP plasma levels resulting from a given 5-HTP dose, by inhibiting the enzyme aromatic amino acid decarboxylase. PDIs at therapeutic doses do not penetrate the brain to any functional degree. 5-HTP conversion to 5-HT is therefore inhibited only in the periphery. This allows more 5-HTP to enter the brain for conversion to 5-HT. Simultaneously, adverse events caused by 5-HTP to 5-HT conversion in the periphery—e.g. diarrhea from 5-HTP conversion to 5-HT in the intestine—can be further minimized. Non-exhaustive examples of PDIs include carbidopa and benserazide. The clinical use of oral PDIs to enhance 5-HTP plasma exposure is well described in the art and will be understood by the practitioner (Gijsman et al, 2002; Turner et al, 2006). Accordingly, in some embodiments, the method further comprises administering a PDI to the subject. In some embodiments, the method is free of administration of a PDI.

In some embodiments, an anti-emetic is co-administered with the 5-HTP, either in the same IV solution, in a different IV solution, or in a different dosage form, non-exhaustive examples of which includes a tablet, capsule, patch, or an IV, intramuscular (IM), or subcutaneous (SC) infusion/injection. The anti-emetic can be used to prevent or attenuate nausea and vomiting, the more prevalent adverse events mediated predominantly by 5-HTP to 5-HT conversion in the brain. Anti-emetics are well-known in the art and used widely in human therapy. Non-exhaustive examples of anti-emetics include $5-HT_3$ receptor antagonists, neurokinin 1 receptor antagonists, dopamine receptor antagonists, antihistamines, corticosteroids, cannabinoids, benzodiazepines, and anti-cholinergics (Dulay and Dulay, 2020). Exemplary $5-TH_3$ receptor antagonists include, but are not limited to, ondansetron, granisetron, palonosetron, dolasetron, tropisetron, and ramosetron.

The infusion of 5-HTP, and of additional optional ancillary drugs (e.g., an anti-emetic or PDI), can be achieved via an IV bag paired with a flow-regulating device, e.g. pump. In some embodiments the infusions are achieved using a pump with a reservoir. In some embodiment the pump and/or reservoir are wearable, and in some embodiments the wearable pump and reservoir is an integrated unit. Devices to achieve the foregoing types of infusions are well-known in the art (Tang et al, 2002). See also, for example, U.S. Pat. No. 4,191,184, the disclosure of which is incorporated by reference in its entirety.

In some embodiments, a transient or average 5-HTP infusion rate during the continuous IV infusion ranges from about 0.005 milligrams per kilogram body weight per hour (mg/kg/hr) to about 5 mg/kg/hr (i.e., about 0.12 milligrams per kilogram body weight per day (mg/kg/24 hr) to about 120 mg/kg/24 hr). In some embodiments, a transient or average 5-HTP infusion rate is about 0.005 mg/kg/hr to about 1.5 mg/kg/hr (i.e., about 0.12 mg/kg/24 hr to about 36 mg/kg/24 hr). In some embodiments, a transient or average 5-HTP infusion rate is about 0.6 mg/kg/24 hr to about 10 mg/kg/24 hr (e.g., about 1, 2, 3, 4, 5, 6, 7, 8, 9, or 10 mg/kg/24 hr).

In some embodiments, the average 5-HTP infusion rate during the continuous IV infusion is from about 0.005 (mg/kg/hr) to about 0.250 mg/kg/hr (i.e., about 0.12 mg/kg/

24 hr to about 6 mg/kg/24 hr). In some embodiments, the average 5-HTP infusion rate is about 0.010 mg/kg/hr to about 0.125 mg/kg/hr (i.e., about 0.25 mg/kg/24 hours to about 3 mg/kg/24 hr). Thus, in some embodiments, the average 5-HTP infusion rate is about 0.0104 mg/kg/hr (i.e., about 0.25 mg/kg/24 hr), about 0.0208 mg/kg/hr (i.e., about 0.5 mg/kg/24 hr), about 0.0417 mg/kg/hr (i.e., about 1 mg/kg/24 hr), about 0.0833 mg/kg/hr (i.e., about 2 mg/kg/24 hr), or about 0.125 mg/kg/hr (i.e., about 3 mg/kg/hr). Infusion regimens including ramp-up or ramp-downs can include temporary 5-HTP infusion rates above or below these ranges.

Infusion volume rates typically range from about 0.4 milliliters per hour (ml/h) to about 80 ml/h. In some embodiments, the infusion volume rate is about 4 ml/h to about 40 ml/h. Infusion regimens including ramp-up or ramp-downs can include temporary infusion volume rates above or below these ranges.

The aqueous solubility of 5-HTP is approximately 10 mg/ml. However, 5-HTP has been reported to be soluble to up to about 100 mg/ml in some solvents (Jacobsen et al, 2016a). In some embodiments, the concentration of 5-HTP in the infusion solutions (i.e., the infusate fluids) is between about 1 mg/ml and about 10 mg/ml. In some embodiments, the concentration is between about 0.1 mg/ml and about 1 mg/ml. In some embodiments, the concentration is between about 10 mg/ml and about 100 mg/ml.

In some embodiments the continuous IV 5-HTP infusion is used as monotherapy to treat a disorder (e.g., suicidal ideation). In some embodiments the continuous IV 5-HTP infusion is used together with another drug or drugs to treat a disorder, and without directly interacting pharmacodynamically with said drug or drugs. In some embodiments the continuous IV 5-HTP infusion is used together with another drug or drugs to treat a disorder (e.g., a neurological or psychiatric disorder), and in a fashion so that the continuous IV 5-HTP infusion interacts pharmacodynamically with said other drug or drugs. For the latter, in some embodiments, the drug or drugs the continuous IV 5-HTP infusion interacts pharmacodynamically with is a $5\text{-}HT_{Ext}$-elevating drugs, such as a serotonin reuptake inhibitor (e.g., a selective serotonin reuptake inhibitor (SSRI), a serotonin noradrenaline reuptake inhibitor (SNRI), a tricyclic antidepressant (TCA)), a monoamine oxidase inhibitor (MAOI), or a 5-HT receptor modulator.

In some embodiments, the pharmacodynamic interaction between the continuous IV 5-HTP infusion and one or more other drugs in treating a disorder (e.g., a neurological or psychiatric disorder) involves elevation of brain $5\text{-}HT_{Ext}$ either in an additive or in a synergistic fashion, e.g., so that the brain $5\text{-}HT_{Ext}$-elevation after continuous IV 5-HTP infusion and administration of the other drug is higher than the sum of each treatments effect alone. In some embodiments, the pharmacodynamic interaction between the continuous IV 5-HTP infusion and one or more other drugs in treating a disorder (e.g., a neurological or psychiatric disorder) involves the one or more other drugs having been administered to the patient for day(s), one week, several weeks, months, or years before the initiation of the continuous IV 5-HTP infusion.

In some embodiments, the terms "patient" and "subject in need" according to the presently disclosed subject matter are defined as any human or mammal that would benefit from the continuous IV 5-HTP infusion in eliminating or lessening the symptoms from a disorder (e.g., a neurological or psychiatric disorder). Thus, the terms "patient" and "patients" include references to mammalian (e.g., human) patients. As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment by virtue of having been diagnosed with a neurological or psychiatric disorder or who is suspected of having such a disorder or a recurrence of such a disorder.

In some embodiments, the continuous IV 5-HTP infusion can be effective in treating neurological or psychiatric disorders. In some embodiments, the neurological or psychiatric disorder is selected from the group comprising depression, social anxiety, panic disorder, generalized anxiety disorder, obsessive-compulsive disorder (OCD), impulse control disorders, suicidal ideation, borderline personality disorder, fibromyalgia, ataxia, mood symptoms and agitation related to neurological disorders (e.g. Alzheimer's, Parkinson's), stroke recovery, autism, migraine, sleep disorders, premenstrual dysphoria, post-traumatic stress disorder (PTSD), post-partum depression, and depression after interferon treatment.

In some embodiments, the continuous IV 5-HTP infusion is used to treat a psychological disorder, such as suicidal ideation, a mood disorder (e.g., depression, bipolar disorder, post-partum depression, or depression after interferon treatment), an anxiety disorder (e.g., social anxiety, panic disorder, generalized anxiety, OCD, or PTSD), or an impulse control disorder.

In some embodiments, the condition treated with the continuous IV 5-HTP infusion is acute suicidal ideation. In some embodiments, the subject in need of treatment for acute suicidal ideation is a subject presenting in a hospital and in need of acute care. For example, acute suicidal ideation can refer to an onset or increase in symptoms (i.e., thoughts about death, planning and/or actions) within the last about 7 days.

In some embodiments, the condition treated with the continuous IV 5-HTP infusion is chronic suicidal ideation (i.e., chronic suicidal ideation and/or behaviors). In some embodiments, a subject in need of treatment for chronic suicidality is a subject presenting at a health care provider and in need of chronic care.

In some embodiments, the continuous IV 5-HTP infusion occurs fully in an in-patient setting (e.g., in a hospital or nursing home). In some embodiments, the continuous IV 5-HTP infusion occurs fully in an outpatient setting (e.g., in a clinic, a doctor's office, or in the patient's home). In some embodiments, the continuous IV 5-HTP infusion occurs partially in an in-patient setting, partially in an outpatient setting. For example, the infusion could be initiated by an emergency medical technician (EMT), nurse, or doctor, in a patient's home and continued during transfer and after arrival at a medical facility (e.g., a hospital). In some embodiments, the out-patient setting is away from a healthcare facility, e.g., in the patient's home.

In accordance with the foregoing, there is provided a method of treating a patient suffering from a psychiatric disorder using a continuous IV infusion of 5-HTP. In some embodiments the patient is in an acute psychiatric crisis, non-exhaustive examples of which includes acute suicidal ideation, acute worsening of a mood disorder, acute worsening of an anxiety disorder, acute worsening of obsessive-compulsive disorder, and acute worsening of an impulse control disorder. In some embodiments the patient is suffering from an ongoing psychiatric disorder deemed in need of treatment using a continuous IV 5-HTP infusion, non-exhaustive examples of which include suicidal ideation, a mood disorder, an anxiety disorder, and an impulse control disorder.

In some embodiments, the patient is treated with the continuous IV 5-HTP infusion without subsequent follow-up therapy. In some embodiments, the patient is treated with a follow-up therapy. In some embodiments, the follow-up therapy is an oral 5-HTP treatment, for instance an oral 5-HTP slow-release drug. In some embodiments, the therapy with an oral 5-HTP slow-release drug is begun in an inpatient setting. In some embodiments, the therapy with an oral 5-HTP slow-release drug is begun in an outpatient setting. In some embodiments, the oral 5-HTP slow-release drug is a gastroretentive dosage form. In some embodiments, the oral 5-HTP slow-release drug contains a PDI. In some embodiments, the follow-up therapy is standard-of-care. In some embodiments, the follow-up therapy is a drug treatment, psychotherapy, and/or brain stimulation therapy.

In accordance with the foregoing, there is provided a method of treating a patient suffering from a neurological disorder using a continuous IV infusion of 5-HTP, with or without follow-up therapy. Non-exhaustive examples of potentially treatable neurological disorders include fibromyalgia, ataxia, mood symptoms and agitation related to neurological disorders (e.g., Alzheimer's, Parkinson's), stroke recovery, migraine, sleep disorders, and phenylketonuria.

In some embodiments, the presently disclosed subject matter provides a pharmaceutical composition for use in treating a neurological or psychiatric disorder in a subject in need of treatment thereof, wherein the pharmaceutical composition comprises an infusate fluid comprising 5-HTP. In some embodiments, the infusate fluid comprises a pharmaceutically acceptable carrier, such as an aqueous solvent (e.g., water or saline). In some embodiments, the 5-HTP infusate fluid of the presently disclosed subject matter comprises an aqueous isotonic solution having osmolarity of about 300 mOsm and a pH of 4-8.

In some embodiments, the presently disclosed subject matter provides a method of elevating brain 5-HT$_{Ext}$ in a subject in need thereof, wherein the method comprises administering 5-HTP to the subject as a continuous IV infusion over an infusion treatment period lasting about four hours or more wherein the administering provides a 5-HTP plasma exposure (as an area under plasma concentration versus time curve extrapolated to infinity (AUC$_{Inf}$, in hours times ng/ml)) of about 3500 times the total dose of 5-HTP (in mg 5-HTP per kilogram kg body weight). In some embodiments, the 5-HTP infusion rate to provide the 5-HTP AUC$_{Ext}$ is about 0.010 milligrams per kilogram body weight per hour (mg/kg/h) to about 0.125 mg/kg/h on average over the infusion treatment period (e.g., about 0.0104 mg/kg/h, about 0.0208 mg/kg/h, about 0.419 mg/kg/h, about 0.0833 mg/kg/h, or about 0.125 mg/kg/b on average over the infusion treatment period).

In some embodiments, the infusion treatment period is between about 4 hours and about 24 hours (e.g., about 4, 5, 6, 7, 8, 9, 10, 11, 12, 13, 14, 15, 16, 17, 18, 19, 20, 21, 22, 23, or about 24 hours). In some embodiments, the infusion treatment period is about 24 hours. In some embodiments, the infusion treatment period is greater than about 24 hours (e.g., about 25 hours to about 144 hours or about 25 hours to about 36 hours).

In some embodiments, the continuous IV infusion is performed at a constant infusion volume rate, wherein the volume of infusate fluid administered to the subject per unit time (e.g., in ml/h) remains the same over the entire infusion treatment period. In some embodiments, the continuous IV infusion is performed at a variable infusion volume rate. As noted hereinabove, in some embodiments, the infusion volume rates range from about 0.4 ml/h to about 80 ml/h. In some embodiments, the infusion volume rate is about 4 ml/h to about 60 ml/h (e.g., about 5 ml/h, about 10 ml/h, about 15 ml/h, about 20 mi/h, about 25 mi/h, about 30 mi/h, about 35 mi/h, about 40 mi/h, about 45 mi/h, about 50 ml/h, about 55 m/h, or about 60 mi/h).

In some embodiments, the continuous IV infusion is performed at a constant volume rate of about 4 mi/h to about 10 ml/h (e.g., about 4, 5, 6, 7, 8, 9, or 10 ml/h) and using infusate fluid of constant 5-HTP concentration. In some embodiments, the continuous IV infusion is performed at a variable infusion volume rate and using an infusate fluid of constant 5-HTP concentration. Thus, in some embodiments, e.g., using infusate fluid of a single 5-HTP concentration, the continuous IV infusion is performed at a first infusion volume rate for a first portion of the infusion treatment period and at a second infusion volume rate for a second portion of the infusion treatment period, wherein the first infusion volume rate is lower than the second infusion volume rate. In some embodiments the continuous IV infusion is performed at three, four or more different infusion volume rates over the course of the infusion treatment period. In some embodiments, the infusion volume rate increases in a step-wise manner over the course of the infusion treatment period, decreases in a step-wise manner over the course of the infusion treatment period, or first increases in a step-wise manner and then decreases in a step-wise manner over the course of the infusion treatment period).

In some embodiments, the continuous IV infusion is performed, e.g., using infusate fluid of constant 5-HTP concentration, at four different infusion volume rates over the course of an infusion treatment period: a first infusion volume rate for a first portion of the infusion treatment period, a second infusion volume rate for a second portion of the infusion treatment period, a third infusion volume rate for a third portion of the infusion treatment period, and a fourth infusion volume rate for a fourth portion of the infusion treatment period. In some embodiments, each portion of the infusion treatment period is the same (i.e., the same amount of time). In some embodiments, the portions of the infusion treatment period are different. In some embodiments, the infusion volume rate is gradually ramped up, e.g., so that when there are four infusion volume rates, the first infusion volume rate is the lowest infusion volume rate, the second infusion volume rate is the next lowest infusion volume rate, the third infusion volume rate is the second highest rate and the fourth infusion volume rate is the highest infusion volume rate. In some embodiments, e.g., using the same infusate solution (i.e., so that the concentration of 5-HTP in the infusate solution remains constant), the first infusion volume rate is between about 10 ml/h and about 20 ml/h, the second infusion volume rate is higher than the first infusion volume rate and is between about 20 ml/h and about 35 ml/h, the third infusion volume rate is higher than the second infusion volume rate and is about 35 ml/h to about 45 ml/h, and the fourth infusion volume rate is higher than the third infusion volume rate and is about 45 ml/h to about 60 ml/h. In some embodiments, the first, second and third portions of the infusion treatment period are each about the same (e.g., about 4 hours). In some embodiments, the fourth portion of the infusion treatment period is the longest portion of the infusion treatment period.

In some embodiments, the fourth portion of the infusion treatment period is about half of the infusion treatment period (e.g., about 12 hours).

As noted above, a transient or average 5-HTP infusion rate during the continuous IV infusion can range from about 0.005 milligrams per kilogram body weight per hour (mg/kg/h) to about 5 mg/kg/h (i.e., about 0.12 milligrams per kilogram body weight per day (mg/kg/24 hr) to about 120 mg/kg/24 hr). In some embodiments, a transient or average 5-HTP infusion rate is about 0.025 to about 1.5 mg/kg/h (i.e., about 0.6 mg/kg/24 hr to about 36 mg/kg/24 hr). In some embodiments, a transient or average 5-HTP infusion rate is about 0.6 mg/kg/24 h to about 10 mg/kg/24 h (e.g., about 1, 2, 3, 4, 5, 6, 7, 8, 9, or 10 mg/kg/24 hr). In some embodiments, a transient or average 5-HTP infusion rate is about 1 mg/kg/24 hr to about 3 mg/kg/24 hr. In some embodiments, a transient or average 5-HTP infusion rate is about 1 mg/kg/24 hr or about 3 mg/kg/24 hr. In some embodiments, a transient or average 5-HTP infusion rate is about 1 mg/kg/24 hr. In some embodiments, a transient or average 5-HTP infusion rate is about 2 mg/kg/24 hr. In some embodiments, a transient or average 5-HTP infusion rate is about 3 mg/kg/24 hr.

In some embodiments, the average or constant 5-HTP infusion rate is about 0.005 milligrams per kilogram body weight per hour (mg/kg/hr) to about 0.250 mg/kg/hr (i.e., about 0.12 milligrams per kilogram body weight per 24 hours or per day (mg/kg/24 hr) to about 6 mg/kg/24 hr). In some embodiments, the average or constant 5-HPT infusion rate is about 0.010 mg/kg/hr to about 0.125 mg/kg/hr (i.e., about 0.25 mg/kg/24 hr to about 3 mg/kg/24 hr).

In some embodiments, the continuous IV infusion is performed at a constant 5-HTP infusion rate, wherein the amount of 5-HTP administered to the subject per unit time (e.g., the mg/kg/hr or mg/kg/24 hr) remains the same over the entire infusion treatment period. In some embodiments, the continuous IV infusion is performed at a variable 5-HTP infusion rate, wherein the amount of 5-HTP administered per unit time is variable over the course of the infusion treatment period (e.g., wherein the 5-HTP infusion is performed using a series of different transient 5-HTP infusion rates over the infusion treatment period). In some embodiments, the constant 5-HTP infusion rate is from about 0.005 mg/kg/hr to about 0.250 mg/kg/hr (i.e., about 0.12 mg/kg/24 hr to about 6 mg/kg/24 hr). In some embodiments, the constant 5-HTP infusion rate is about 0.010 mg/kg/hr to about 0.125 mg/kg/hr (i.e., about 0.25 mg/kg/24 hours to about 3 mg/kg/24 hr). In some embodiments, the constant 5-HTP infusion rate is about 0.0104 mg/kg/hr (i.e., about 0.25 mg/kg/24 hr), about 0.0208 mg/kg/hr (i.e., about 0.5 mg/kg/24 hr), about 0.0417 mg/kg/hr (i.e., about 1 mg/kg/24 hr), about 0.0833 mg/kg/hr (i.e., about 2 mg/kg/24 hr), or about 0.125 mg/kg/hr (i.e., about 3 mg/kg/hr).

In some embodiments, the continuous IV infusion is performed at a variable infusion rate (e.g., so that the average 5-HTP infusion rate is from about 0.005 mg/kg/hr to about 0.250 mg/kg/hr or about 0.0107 mg/kg/hr to about 0.125 mg/kg/hr over the course of the infusion treatment period). The variable 5-HTP infusion rate can be provided by using a variable infusion volume rate of a single infusate fluid over the course of the continuous infusion, by changing the 5-HTP concentration of the infusate fluid during the course of the continuous infusion, or by a combination of changing the infusion volume rate and changing the 5-HTP concentration of the infusate fluid during the course of the continuous infusion. Thus, in some embodiments, the continuous IV infusion is performed at a first 5-HTP infusion rate for a first portion of the infusion treatment period and at a second 5-HTP infusion rate for a second portion of the infusion treatment period, wherein the first 5-HTP infusion rate is lower than the second 5-HTP infusion rate. In some embodiments the continuous IV infusion is performed at three, four or more different 5-HTP infusion rates over the course of the infusion treatment period. In some embodiments, the 5-HTP infusion rate increases in a step-wise manner over the course of the infusion treatment period, decreases in a step-wise manner over the course of the infusion treatment period, or first increases in a step-wise manner and then decreases in a step-wise manner over the course of the infusion treatment period)

In some embodiments, the continuous IV infusion is performed at four different 5-HTP infusion rates (i.e., four different transient infusion rates) over the course of an infusion treatment period: a first 5-HTP infusion rate for a first portion of the infusion treatment period, a second 5-HTP infusion rate for a second portion of the infusion treatment period, a third 5-HTP infusion rate for a third portion of the infusion treatment period, and a fourth 5-HTP infusion rate for a fourth portion of the infusion treatment period. In some embodiments, each portion of the infusion treatment period is the same (i.e., the same amount of time). In some embodiments, the portions of the infusion treatment period are different. In some embodiments, the 5-HTP infusion rate is gradually ramped up, e.g., so that when there are four 5-HTP infusion rates, the first 5-HTP infusion rate is the lowest 5-HTP infusion rate, the second 5-HTP infusion rate is the next lowest 5-HTP infusion rate, the third 5-HTP infusion rate is the second highest 5-HTP infusion rate and the fourth 5-HTP infusion rate is the highest 5-HTP infusion rate.

In some embodiments, e.g., when the 5-HTP infusion rate is a constant 5-HTP infusion rate, the administering provides a steady state 5-HTP plasma level in about 4 to about 6 hours. In some embodiments, the steady state 5-HTP plasma level is provided in about 4 hours. In some embodiments, the 5-HTP infusion rate (e.g., the constant 5-HTP infusion rate) is about 1 mg/kg/24 hr and the administering provides a steady state 5-HTP plasma level of about 100 ng/ml. In some embodiments, the 5-HTP infusion rate (e.g., the constant 5-HTP infusion rate) is about 0.5 mg/kg/24 hr and the administering provides a steady state 5-HTP plasma level of about 50 ng/ml. In some embodiments, the 5-HTP infusion rate (e.g., the constant 5-HTP infusion rate) is about 0.25 mg/kg/24 hr and the administering provides a steady state 5-HTP plasma level of about 25 ng/ml. In some embodiments, the 5-HTP infusion rate (e.g., the constant 5-HTP infusion rate) is about 2 mg/kg/24 hr and the administering provides a steady state 5-HTP plasma level of about 200 ng/ml. In some embodiments, the 5-HTP infusion rate (e.g., the constant 5-HTP infusion rate) is about 3 mg/kg/24 hr and the administering provides a steady state 5-HTP plasma level of about 300 ng/ml.

In some embodiments, e.g., when using a constant 5-HTP infusion rate, the infusion treatment period is about 4 hours or more, the 5-HTP infusion rate (e.g., the constant 5-HTP infusion rate) is about 0.0417 mg/kg/hr, and the administering provides a steady state 5-HTP plasma level of about 100 ng/ml. In some embodiments, the infusion treatment period is about 4 hours or more, the 5-HTP infusion rate (e.g., the constant 5-HTP infusion rate) is about 0.0208 mg/kg/hr, and the administering provides a steady state 5-HTP plasma level of about 50 ng/ml. In some embodiments, the infusion treatment period is about 4 hours or more, the 5-HTP infusion rate (e.g., the constant 5-HTP infusion rate) is about 0.0104 mg/kg/hr, and the administering provides a steady state 5-HTP plasma level of about 25 ng/ml. In some embodiments, the infusion treatment period is about 4 hours or more, the 5-HTP infusion rate (e.g., the constant 5-HTP infusion rate) is about 0.0833 mg/kg/hr, and the administering provides a steady state 5-HTP plasma level of about 200 ng/ml. In some embodiments, the infusion treatment period is about 4 hours or more, the 5-HTP infusion rate (e.g., the constant 5-HPT infusion rate) is about 0.125 mg/kg/hr, and the administering provides a steady state 5-HTP plasma level of about 300 ng/ml.

In some embodiments, the infusion treatment period is about 4 hours or more and the ratio of steady state 5-HTP plasma levels (in ng/ml) to 5-HTP dose (in mg/kg/hr) is about 2400.

In some embodiments, the method further comprises administering to the subject an extracellular 5-HT (5-HT$_{Ext}$)-elevating compound, together with the continuous 5-HTP infusion of a duration of about 4 hours or more. The term "5-HT$_{Ext}$-elevating compound" refers to any compound that increases, directly or indirectly, the availability of 5-HT in the central nervous system for binding to 5-HT receptors and hence enhancing 5-HT neurotransmission. 5-HT$_{Ext}$-elevating (or serotonin-enhancing) compounds (and salts and solvates thereof) suitable for use as additional therapeutic agents according to the presently disclosed subject matter include, but are not limited to, selective serotonin reuptake inhibitors (SSRIs), serotonin-norepinephrine reuptake inhibitors (SNRIs), tricyclic antidepressants (TCAs), atypical antidepressants, and monoamine oxidase inhibitors (MAOIs).

The term "SSRI" or "selective serotonin reuptake inhibitor" refers to those compounds typically used as antidepressants and are associated with the increase in the extracellular level of the neurotransmitter serotonin (i.e., 5-HT) by inhibiting its uptake into the presynaptic cell, increasing the level of 5-HT in the synaptic cleft (i.e., 5-HT$_{Ext}$) available to bind to the postsynaptic receptor. Examples of suitable SSRIs include, but are not limited to, citalopram, dapoxetine, escitalopram, fluoxetine, fluvoxamine, indalpine, paroxetine, sertraline, vilazodone, zimelidine and combinations thereof. In some embodiments, the SSRI is escitalopram. Examples of MAOIs include, but are not limited, to isocarboxazid, phenelzine, tranylcypromine, moclobemide, and phenethylamines such as selegiline. Additional compounds suitable for use in the presently disclosed methods as 5-HT$_{Ext}$-elevating compounds include, but are not limited to, tricyclic antidepressants, such as, but not limited to, imipramine, amitriptyline, and clomipramine; amphetamine, including, but not limited to, derivatives thereof such as phentermine, fenfluramine, and (+)-3,4-methylenedioxyamphetamine; SNRIs, such as venlafaxine and duloxetine, as well as vortioxetine and vilazodone.

In some embodiments, the 5-HT$_{Ext}$-elevating compound is a serotonin reuptake inhibitor (e.g., a SSRI, such as, but not limited to, escitalopram). In some embodiments, the subject is being simultaneously or concurrently treated with the serotonin reuptake inhibitor (or other 5-HT$_{Ext}$-elevating compound) and/or has been pre-treated with the serotonin reuptake inhibitor (or other 5-HT$_{Ext}$-elevating compound), i.e., administered the serotonin reuptake inhibitor using a standard dosage or administration schedule for that inhibitor, for at least one week, at least two weeks, at least three weeks, at least four weeks, or more prior to the initiation of the continuous IV infusion of 5-HTP. By simultaneously or concurrently treated is meant, for example, a subject who has received a dose of the serotonin reuptake inhibitor on the same day or within about 24 hours or 48 hours, as the initiation of the continuous IV infusion of 5-HTP. In some embodiments, the subject is a subject who has been pre-treated with and is being simultaneously/concurrently being treated with a serotonin reuptake inhibitor.

An increase in plasma (or serum or saliva) cortisol after a 5-HT$_{Ext}$-elevating compound signifies an elevation of brain 5-HT$_{Ext}$, as a cortisol increase in this context is a biomarker of brain 5-HT$_{Ext}$-elevation. In some embodiments, the administering of the continuous IV infusion of 5-HTP provides an increase in cortisol concentration in a subject pretreated and/or simultaneously treated with a 5-HT$_{Ext}$-elevating compound compared to if that subject were not administered the continuous IV infusion of 5-HTP. In some embodiments, the administering of the continuous IV infusion of 5-HTP provides an increase in plasma (or serum or saliva) cortisol concentration in a subject not pretreated with a 5-HT$_{Ext}$-elevating compound. In some embodiments, when a subject is pretreated and/or simultaneously treated with a 5-HT$_{Ext}$-elevating compound, a lower 5-HTP infusion dose or lower 5-HTP infusion rate can elevate cortisol as compared to the dose or infusion rate used when the subject is not pretreated and/or simultaneously treated with a 5-HT$_{Ext}$-elevating compound.

In some embodiments, the method (i.e., the administration of the 5-HTP via continuous IV infusion, such as the administration of 5-HTP via continuous IV infusion to a subject being treated with and/or who has been pretreated with a 5-HT$_{Ext}$-elevating compound (e.g., a SSRI)) is free of severe and moderate adverse effects. Accordingly, in some embodiments, the presently disclosed subject matter provides rapid onset (e.g., within less than 1 week or 1 day) of therapeutic levels of 5-HTP while at the same time avoiding moderate or severe AEs, including those typically associated with excessive 5-HT stimulation, e.g., moderate or severe nausea, vomiting, diarrhea, somnolence, gastrointestinal upset, and/or dizziness. In some embodiments, the average 5-HTP infusion rate is 1 mg/kg/24 hr (i.e., about 0.0417 mg/kg/hr) or less (e.g., about 0.25 mg/kg/24 hr to about 1 mg/kg/24 hr, i.e., about 0.0104 mg/kg/hr to about 0.0417 mg/kg/hr) and the method is free of moderate and severe AEs associated with the IV administration of 5-HTP. In some embodiments, the 5-HTP infusion rate is constant at 1 mg/kg/24 hr (i.e., about 0.0417 mg/kg/hr) or less (e.g., about 0.25 mg/kg/24 hr to about 1 mg/kg/24 hr (i.e., about 0.0104 mg/kg/hr to about 0.0417 mg/kg/hr)) and the meshod is free of moderate and severe AEs associated with the IV administration of 5-HTP.

In some embodiments, the method further comprises co-administering to the subject a PDI, such as a PDI as described above. In some embodiments, the method is free of administering (e.g., is free of co-administering) a PDI to the subject.

In some embodiments, the method further comprises administering to the subject an anti-emetic, as described above. As described above, anti-emetics include, but are not limited to, 5-HT$_3$ receptor antagonists, neurokinin 1 receptor antagonists, dopamine receptor antagonists, antihistamines, corticosteroids, cannabinoids, benzodiazepines, and anticholinergics. In some embodiments, the anti-emetic is a 5-HT$_3$ receptor antagonist.

In some embodiments, the subject in need of elevation of brain 5-HT is a human subject. In some embodiments, the subject is a human subject in need of treatment for a neurological or psychiatric disorder, such as, but not limited to, depression, social anxiety, panic disorder, generalized anxiety disorder, obsessive-compulsive disorder (OCD), impulse control disorders, suicidal ideation, borderline personality disorder, fibromyalgia, ataxia, mood symptoms and agitation related to neurological disorders (e.g. Alzheimer's, Parkinson's), stroke recovery, autism, migraine, sleep disorders, premenstrual dysphoria, post-traumatic stress disorder (PTSD), post-partum depression, and depression after interferon treatment. In some embodiments, the neurological or psychiatric disorder is suicidal ideation or acute worsening of a mood disorder. In some embodiments, the disorder is acute suicidal ideation.

In some embodiments, the method further comprises administering an additional treatment to the subject after completion of the infusion treatment period. For instance, the additional treatment can be administered to maintain the therapeutic effect (e.g., improvement of symptoms) resulting from the administration of the continuous IV infusion of 5-HTP. In some embodiments, the additional treatment is the administration of a slow-release formulation comprising 5-HTP (e.g., a slow-release oral formulation of 5-HTP). In some embodiments, the initiation of administration of the additional treatment is within about 24 hours (e.g., within about 2, 4, 6, 8, 10, 12, 14, 16, 20, or 24 hours) of the completion of the infusion treatment period.

In some embodiments, the presently disclosed subject matter provides a composition for use in treating a neurological or psychiatric disorder, such as for use in treating suicidal ideation or acute worsening of a mood disorder, wherein the composition comprises 5-HTP and is administered as a continuous IV infusion over an infusion time period lasting about 4 hours or more, wherein the administering provides a 5-HTP plasma exposure, as an $AUC_{Inf}$ (in hours times ng/ml), of about 3500 times the total dose of 5-HTP (in mg 5-HTP per kg body weight). In some embodiments, the 5-HTP infusion rate to provide the 5-HTP $AUC_{Inf}$ is about 0.010 milligrams per kilogram body weight per hour (mg/kg/hr) to about 0.125 mg/kg/hr on average over the infusion treatment period (e.g., about 0.0104 mg/kg/hr, about 0.0208 mg/kg/hr, about 0.0417 mg/kg/hr, about 0.0833 mg/kg/hr, or about 0.125 mg/kg/hr on average over the infusion treatment period). In some embodiments, the composition is for use in a method where the 5-HTP infusion rate is constant throughout the infusion treatment period. In some embodiments, the composition is for use in a method where the continuous IV infusion is performed at a variable 5-HTP infusion rate, yielding differing mg/kg drug delivery rates at different particular time points within the infusion time period. For instance, in some embodiments, the continuous IV infusion is performed at a first infusion rate for a first portion of the infusion treatment period and at a second infusion rate for a second portion of the infusion treatment period, wherein the first infusion rate is lower than the second infusion rate. However, the continuous IV infusion can be performed at more than two different 5-HTP infusion rates and the 5-HTP infusion rates can be gradually ramped down or up, e.g., as described above. Suitable infusion rates (e.g., average, constant, or transient) for constant and variable rate 5-HTP infusion profiles are described above.

In some embodiments, the composition is for use in a method where the average 5-HTP infusion rate is about 1 mg/kg/24 hr to about 3 mg/kg/24 hr. In some embodiments, the average 5-HTP infusion rate is about 1 mg/kg/24 hr. about 2 mg/kg/24 hr or about 3 mg/kg/24 hr. In some embodiments, the average 5-HTP infusion rate is about 1 mg/kg/24 hr. In some embodiments, the average 5-HTP infusion rate is about 2 mg/kg/24 hr. In some embodiments, the average 5-HTP infusion rate is about 3 mg/kg/24 hr.

In some embodiments, the composition is for use in a method where the infusion treatment period is about 4 hours to about 24 hours (e.g., about 4, 6, 8, 10, 12, 14, 16, 18, 20, 22, or about 24 hours). In some embodiments the infusion treatment period is about 24 hours. In some embodiments, the infusion treatment period is greater than about 24 hours (e.g., about 36 hours or about 48 hours).

In some embodiments, e.g., when the composition is used in a method wherein continuous IV infusion is performed at a constant 5-HTP infusion rate, the 5-HTP infusion rate (e.g., the constant 5-HTP infusion rate) is about 1 mg/kg/24 hr and the administering provides a steady state 5-HTP plasma level of about 100 ng/ml. In some embodiments, the 5-HTP infusion rate (e.g., the constant 5-HTP infusion rate) is about 0.5 mg/kg/24 hr and the administering provides a steady state 5-HTP plasma level of about 50 ng/ml. In some embodiments, the 5-HTP infusion rate (e.g., the constant 5-HTP infusion rate) is about 0.25 mg/kg/24 hr and the administering provides a steady state 5-HTP plasma level of about 25 ng/ml. In some embodiments, the 5-HTP infusion rate (e.g., the constant 5-HTP infusion rate) is about 2 mg/kg/24 hr and the administering provides a steady state 5-HTP plasma level of about 200 ng/ml. In some embodiments, the 5-HTP infusion rate (e.g., the constant 5-HTP infusion rate) is about 3 mg/kg/24 hr and the administering provides a steady state 5-HTP plasma level of about 300 ng/ml.

In some embodiments, e.g., when the IV infusion is performed using a constant 5-HTP infusion rate, the infusion duration is about 4 hours or more, the 5-HTP infusion rate is about 0.0417 mg/kg/hr and the administering provides a steady state 5-HTP plasma level of about 100 ng/ml. In some embodiments, the infusion duration is about 4 hours or more, the 5-HTP infusion rate (e.g., the constant 5-HTP infusion rate) is about 0.0208 mg/kg/hr and the administering provides a steady state 5-HTP plasma level of about 50 ng/ml. In some embodiments, the infusion duration is about 4 hours or more, the 5-HTP infusion rate (e.g., the constant 5-HTP infusion rate) is about 0.0104 mg/kg/hr and the administering provides a steady state 5-HTP plasma level of about 25 ng/ml. In some embodiments, the infusion duration is about 4 hours or more, the 5-HTP infusion rate (e.g., the constant 5-HTP infusion rate) is about 0.0833 mg/kg/hr and the administering provides a steady state 5-HTP plasma level of about 200 ng/ml. In some embodiments, the infusion duration is about 4 hours or more, the 5-HTP infusion rate (e.g., the constant 5-HTP infusion rate) is about 0.125 mg/kg/hr and the administering provides a steady state 5-HTP plasma level of about 300 ng/ml.

In some embodiments, the composition is for use in a method that further comprises administering to the subject a $5-HT_{Ext}$-elevating compound, such as a $5-HT_{Ext}$-elevating compound as described hereinabove. For example, in some embodiments, the $5-HT_{Ext}$-elevating compound is a serotonin reuptake inhibitor and the subject is a subject being simultaneously treated with the serotonin reuptake inhibitor and/or a subject who has been pre-treated with the serotonin reuptake inhibitor. In some embodiments, the composition is for use in a method that provides an increase in plasma cortisol concentration in the subject compared to a subject not treated with the continuous IV infusion of 5-HTP. For instance, in some embodiments, the administering of the continuous IV infusion of 5-HTP provides an increase in cortisol concentration in a subject pretreated and/or simultaneously treated with a $5-HT_{Ext}$-elevating compound compared to if that subject were not administered the continuous IV infusion of 5-HTP. In some embodiments, the administering of the continuous IV infusion of 5-HTP provides an increase in plasma (or serum or saliva) cortisol concentration in a subject not pretreated with a 5-HT$_{Ext}$-elevating compound. In some embodiments, when a subject is pretreated and/or simultaneously treated with a 5-HT$_{Ext}$-elevating compound, a lower 5-HTP infusion dose or lower 5-HTP infusion rate can elevate cortisol as compared to the dose or infusion rate used when the subject is not pretreated or simultaneously treated with a 5-HT$_{Ext}$-elevating compound. In some embodiments, the composition is for use in a method that is free of severe and moderate adverse effects. For example, in some embodiments, the composition is for use in a method where the average 5-HTP infusion rate is 1 mg/kg/24 hr (i.e., about 0.0417 mg/kg/hr) or less (e.g., between about 0.25 mg/kg/24 hr and about 1 mg/kg/24 hr (i.e., about 0.0104 mg/kg/hr to about 0.0417 mg/kg/hr)) and the method is free of moderate and severe AEs associated with the IV administration of 5-HTP. In some embodiments, the composition is for use in a method where the 5-HTP infusion rate is constant at 1 mg/kg/24 hr (i.e., about 0.0417 mg/kg/hr) or less (e.g., between about 0.25 mg/kg/24 hr to about 1 mg/kg/24 hr (i.e., about 0.0104 mg/kg/hr to about 0.0417 mg/kg/hr)) and the method is free of moderate and severe AEs associated with the IV administration of 5-HTP.

In some embodiments, the composition is for use in a method that is free of administration of a PDI. In some embodiments, the composition is for use in a method further comprising administering an anti-emetic to the subject. For example, in some embodiments, the anti-emetic is a 5-HT$_3$ receptor antagonist.

In some embodiments, the composition is for use in a method that further comprises the administration of an additional treatment to the subject after completion of the infusion treatment period (e.g., to maintain the therapeutic effect of the continuous IV infusion of 5-HTP). The additional treatment can comprise, for example, administration of a slow-release formulation (e.g., a slow-release oral formulation) comprising 5-HTP. The administration of the additional treatment is initiated within about 24 hours of the completion of the infusion treatment period.

In some embodiments, the presently disclosed subject matter provides a method of preparing an 5-HTP infusate solution for use in a method as described herein, wherein the method comprises providing a stock solution comprising 5-HTP and water that has been stored under an inert gas or nitrogen in the dark at 5° C.; and diluting the stock solution to provide a 5-HTP infusate solution having a 5-HTP concentration and infusate fluid volume suitable for delivering a desired dose of 5-HTP to a subject in need thereof over a desired infusion treatment period (e.g., an infusion treatment period of about 4 hours or more) and at a desired infusion rate. In some embodiments, the stock solution comprising 5-HTP has a 5-HTP concentration of about 5 mg/ml.

In some embodiments of the forgoing the stock solution and diluted solution additionally includes physiological concentrations of sodium chloride. In some embodiments the stock solution and diluted solution is made from Normal Saline (0.9% saline).

In some embodiments, the presently disclosed subject matter provides a kit for use in treating a subject in need of elevation of brain 5-HT$_{Ext}$ or treatment of a neurological or psychiatric disorder (e.g., treatment of suicidal ideation or acute worsening of a mood disorder), wherein the kit comprises a stock solution (e.g., a stable pharmaceutical stock solution) comprising 5-HTP and water stored in an amber vial under an inert gas or nitrogen at 5° C.; and instructions for diluting said stock solution to provide an infusate solution having a 5-HTP concentration and fluid volume suitable for delivering a desired dose of 5-HTP to a subject in need thereof over a desired infusion treatment period (e.g., about 4 hours or more). In some embodiments, the kit further comprises Normal Saline (e.g., for diluting said stock solution).

In some embodiments, the presently disclosed subject matter provides a stable pharmaceutical solution comprising 5-HTP and water that is stable for at least 12 months stored at 5° C. under an inert gas (e.g., argon) or nitrogen in the dark. By "stable" is meant both physical and/or chemical stability. The term "physical stability" refers to maintenance of color and particulate matter. The term "chemical stability" relates to formation of (i) active compound-related impurities in terms of total impurity, single maximum individual impurity and maximum individual unknown impurity, and (ii) assay, i.e., concentration of the active compound, where both related impurities and assay remains within pre-defined specifications, usually specifications acceptable to government regulatory authorities.

In some embodiments, the stable solution is for use in preparing an infusate fluid of 5-HTP, such as for use in a method as described herein, e.g., a method for elevating brain 5-HT$_{Ext}$ in a mammal, such as a method that can provide 5-HTP plasma exposure, as an AUC$_{Ext}$ (in hours times ng/ml), of about 3500 times the dose of 5-HTP (in mg 5-HTP per kg body weight). In some embodiments, the method involves continuous IV infusion over an infusion time period of about 4 hours or more.

In some embodiments, the method comprises continuous IV infusion at a 5-HTP infusion rate of about about 0.010 milligrams per kilogram body weight per hour (mg/kg/h) to about 0.125 mg/kg/h on average over the infusion treatment period (e.g., about 0.0104 mg/kg/h, about 0.0208 mg/kg/h, about 0.419 mg/kg/h, about 0.0833 mg/kg/h, or about 0.125 mg/kg/h on average over the infusion treatment period). In some embodiments, the presently disclosed subject matter provides the stable pharmaceutical solution for use in preparing an infusate fluid for continuous IV infusion for treating suicidal ideation (e.g., acute suicidal ideation) or acute worsening of a mood disorder. In some embodiments, the solution has a 5-HTP concentration of about 5 mg/ml. In some embodiments, the solution comprises less than about 5 parts-per-million (ppm) oxygen.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

5-HTP Stock Solution

Briefly, the formulation of the 5-HTP stock solution was performed by dissolving the drug substance, 5-HTP, and sodium chloride in sterile water for injection. Compounding and aseptic filling of a saline (0.9%) 5-HTP stock solution (5 mg/mL) into 100 mL Type I amber glass serum vials, stoppered with 20 mm stoppers and crimped with 20 mm flip-off seals, was done aseptically. The 5-HTP drug substance can be manufactured via extraction from the seeds of *Griffonia simplicifolia* and commercially sourced (by Linnea S A, Lavertezzo, Switzerland). Compendial methods conducted according to United States Pharmacopeia, (USP) are indicated with "<number>" and USP-grade constituent are indicated with "(USP)". The excipients used in manufacturing of the 5-HTP stock solution were sodium chloride (USP). Water for Injection (WFI, USP), and nitrogen (5.0 ultra-high purity). The manufacturing of the 5-HTP stock solution was carried out in accordance with the current Good Manufacturing Practice (cGMP) regulations and guidelines. The 5-HTP stock solution was manufactured using a series of unit operations including compounding, sterile filtration, filling into vials, stoppering, crimping of stopper seals, inspection, labeling, and secondary packaging. The final formulated 5-HTP for IV infusion stock solution was tested for sterility and bacterial endotoxins. More particular details regarding the preparation of the stock solutions are as follows:

Compounding. The 5-HTP stock solution was prepared in a Class C environment by mixing 5-HTP with a vehicle (WFI) using conventional compounding techniques. Briefly, WFI was added to a depyrogenated glass bottle, with a rotating magnetic stir bar for mixing, and sparged with nitrogen until oxygen content was <5 ppm. Approximately 1/10 volume of the sparged WFI was transferred to a separate depyrogenated glass bottle. The remaining WFI was warmed to 27° C.±2° C. while stirring (100-800 rpm). 5-HTP and sodium chloride was dispensed and added to the warm WFI and mixed until completely dissolved. The solution was brought to target gross weight to achieve a concentration of 5 mg/ml and 0.9% saline with the sparged WFI that was set aside and mixed until the stock solution was clear and homogeneous.

Sterile Filtration. The 5-HTP stock solution was sterilized in a Class A environment using aseptic filtration. The 5-HTP stock solution was protected from light and filtered through two 0.22 um fluorodyne sterile filters connected in series into a filtrate bag using a line pump (100-500 m/min).

Filling & Crimping. The sterile 5-HTP stock solution was supplied in 100 mL quantities, filled into 100 mL amber Type I glass vials inside a laminar flow hood using a filling line. Amber vials were selected to protect the solution from light. The amber vials were filled with 100 ml sterile 5-HTP stock solution and the headspace flushed for 5 sec with nitrogen. The filled amber vials were immediately closed with a 20 mm stopper using sterile forceps. The stopper was over-sealed with an aluminum flip-off cap.

Storage conditions. The 5-HTP stock solution vials were stored in horizontal and upright positions. The upright position served as the control position. The vials in the upright position were only tested if a failure was identified for the vials stored in the horizontal position at specific time points. The 5-HTP stock solution vials were stored in horizontal and upright positions under refrigerated conditions at 5° C.±3° C. and under accelerated conditions at 25° C.±2° C./60%+5% relative humidity (RH) for up to 12 months in the dark.

Controls. In process controls included measuring dissolved oxygen in WFI, check for clarity and homogeneity, prefiltration bioburden, filter integrity testing, filling process weight check, container-closure integrity testing.

Example 2

Release and Stability Testing of Sterile 5-HTP Stock Solution

Methods: Release and stability testing was conducted to determine the identity, assay, and related substances of 5-HTP in the 5-HTP stock solution, using standard HPLC-UV methodology. Appearance, pH (USP <791>), osmolality (USP <785>), particulate matter (USP <788>), sterility (USP <71>), and endotoxins (USP <85>) were also assessed. Bacterial endotoxins specification of no more than 4.0 EU/mL was based on the highest potential dose of 5-HTP for IV infusion, i.e., finally diluted 5-HTP solution for clinical administration, (see Example 3, below) at 2.1 mg/ml (for 30 mg/kg/24 h). Specifications for release and stability testing of clinical batches of 5-HTP stock solution are provided in Table 1, below. The specifications were established based on USP acceptance criteria, available release, and stability data.

Due to an increase in particulate matter in 5-HTP stock solution during stability storage, the number of particles was reported as report results in lieu of the usual Particulate Matter in Injections USP <788> specification of ≥10 μm particle size not more than (NMT) 6000 particles/vial and ≥25 μm particle size NMT 600 particles/vial. An investigation using light microscopy and HPLC analysis found the particles to be predominantly 5-HTP crystals, which, without being bound to any one theory, are believed to form from precipitation of minor amounts (compared to assay specification) of the 5-HTP drug substance. The basis for this alternative reporting includes a reference to USP <788> which states that parenteral products for which the labeling specifies use of a final filter prior to administration are exempt from the requirements of Particulate Matter in Injections <788>, provided that scientific data are available to justify exemption. Accordingly, the 5-HTP stock solution 5 mg/mL, stored in amber vials was filtered prior to dilution and IV administration using a sterile 0.22 μm filter. Particulate matter was removed by this filtration step prior to dilution into sterile IV bags (see Example 3, below). An additional filtration step is performed during the infusion into human subjects via an in-line filter.

Storage and duration: Stability studies were conducted on clinical batches of sterile 5-HTP stock solution for up to 6 months under accelerated storage conditions, 25° C./60% relative humidity (RH) in the dark (see Table 2, below), and for up to 12 months under refrigerated storage condition, 5° C. in the dark. See Table 3, below. 5-HTP stock solution vials were stored in a vertical (upright) position and in a horizontal position under both storage conditions. Stability assessments were conducted on 5-HTP stock solution from vials in the horizontal position. The vials in the upright position were tested at the listed time points only if failure was identified for the vials stored in the horizontal position. For particulate matter assessment, assay, and related substances were tested in (i) unfiltered samples of 5-HTP stock solution and (ii) filtered samples of 5-HTP stock solution, using a 0.22 μm nylon syringe filter.

TABLE 1

| 5-HTP stock solution - Specifications for Release Testing | | | |
|---|---|---|---|
| Test | Acceptance Criteria | Method | Testing (R/S) |
| Appearance | Clear, light yellowish to green solution, essentially free from visible particles | Visual check | R, S |
| Identification: HPLC Retention Time | The retention time of the active main peak in sample matches that of 5-HTP in the standard. | HPLC | R |
| Assay | 90.0%-110.0% of label claim | HPLC | R, S |
| Related Substances | Report Individual Related Substances ≥0.05% Total: Report Results | HPLC | R, S |
| Volume in Container | Meets USP requirements | USP <697> | R |
| pH | 5.0-7.5 | USP <791> | R, S |
| Osmolality | NLT 250 mOsm | USP <785> | R, S |
| Sub-visible Particulate (Particulate Matter in Injections) | Report Results | USP <788> | R, S |
| Sterility | Sterile | USP <71> | R, S |
| Bacterial Endotoxins | NMT 4.0 EU/mL | USP <85> | R |

R: Release,
S: Stability;
NMT = Not More Than;
NLT = Not Less Than

Results & Discussion: Results from the release and stability testing of 5-HTP stock solution clinical batches stored in the horizontal position at 25° C./60% RH are presented in Table 2, below, and batches stored in the horizontal position at 5° C. are presented in Table 3, below. Appearance, pH, osmolality, and assay at 3 months and 6 months compared to initial release testing were well within specifications. Assay decreased slightly over time, and appeared to do so more at 25° C./60% RH compared to 5° C. Total related substances increased over time and appeared to do so more at 25° C./60% RH compared to 5° C. Differences between unfiltered and filtered samples were negligible. Particulate matter increased over time at both 25° C./60% RH and 5° C. Samples from 5-HTP stock solution stored at 25° C./60% RH had 5-15 times more particulate matter than samples stored at 5° C. Filtration effectively removed the particulate matter.

All samples from 5-HTP stock solution stored in the horizontal position at 25° C./60% RH and 5° C. were within specification. Therefore, analysis of 5-HTP stock solution stored in the upright position was not performed. At 12 months, 5-HTP for stock solution stored at 5° C. still met specifications. Overall, 5-HTP stock solution, 5 mg/mL, is stable for up to 12 months at 5° C.±3° C., in the dark.

TABLE 2

| Release and Stability Testing of 5-HTP for IV Infusion Clinical Batch at 25° C./60% RH, horizontal position. | | | | | |
|---|---|---|---|---|---|
| Testing | Method | Specification | Initial | 3 M | 6 M |
| Appearance | ATM-1095 | Clear, light yellowish to green solution essentially free from visible particles | Clear, light yellowish solution, essentially free from visible particles | Clear, yellowish solution, essentially free from visible particles | Clear, yellowish solution, essentially free from visible particles |
| pH | USP<791> | 5.0-7.5 | 6.9 | 5.8 | 6.4 |
| Osmolality | USP<785> | NLT 250 mOsm | 318 mOsm | 305 mOsm | 305 mOsm |
| Assay | ATM-2135 | 90.0%-110.0% of label amount | Filtered: 101.8% Unfiltered: 101.3% | Filtered: 99.6% Unfiltered: 99.9% | Filtered: 99.7% Unfiltered: 98.1% |
| Related Substances (% w/w) | ATM-2135 | Report Results Report Individual Related Substances ≥0.05% | Filtered RRT 0.88: 0.05% RRT 1.28: 0.05% L-Tryptophan: 0.13% Total: 0.23% Unfiltered RRT 1.28: 0.05% L-Tryptophan: 0.12% Total: 0.17% | Filtered RRT 0.83: 0.12% RRT 0.86: 0.05% RRT 1.19: 0.10% RRT 1.55: 0.06% RRT 1.62: 0.16% L-Tryptophan: 0.10% Total: 0.59% Unfiltered RRT 0.83: 0.15% RRT 0.86: 0.07% RRT 1.19: 0.10% RRT 1.55: 0.07% RRT 1.62: 0.18% L-Tryptophan: 0.10% Total: 0.67% | Filtered RRT 0.63: 0.05% RRT 0.69: 0.05% RRT 0.98: 0.06% RRT 1.02: 0.05% RRT 1.12: 0.25% RRT 1.18: 0.06% RRT 1.21: 0.11% RRT 1.34: 0.06% RRT 1.43: 0.09% RRT 1.50: 0.17% L-Tryptophan: 0.10% Total: 1.1% Unfiltered RRT 0.63: 0.07% RRT 0.69: 0.07% RRT 0.98: 0.06% RRT 1.02: 0.06% RRT 1.12: 0.26% RRT 1.18: 0.08% RRT 1.21: 0.10% |

TABLE 2-continued

Release and Stability Testing of 5-HTP for IV Infusion Clinical Batch at 25° C./60% RH, horizontal position.

| Testing | Method | Specification | Initial | 3 M | 6 M |
|---|---|---|---|---|---|
| | | | | | RRT 1.34: 0.06%<br>RRT 1.43: 0.10%<br>RRT 1.50: 0.19%<br>L-Tryptophan: 0.10%<br>Total: 1.2% |
| Particulate Matter | USP <788> | Report Results | Filtered<br>≥10 μm: 7 particles/vial<br>≥25 μm: 0 particles/vial<br>Unfiltered<br>≥10 μm: 3347 particles/vial<br>≥25 μm: 153 particles/vial | Filtered<br>≥10 μm: 233 particles/vial<br>≥25 μm: 7 particles/vial<br>Unfiltered<br>≥10 μm: 402,533 particles/vial<br>≥25 μm: 3447 particles/vial | Filtered<br>≥10 μm: 27 particles/vial<br>≥25 μm: 7 particles/vial<br>Unfiltered<br>≥10 μm: 655,820 particles/vial<br>≥25 μm: 5487 particles/vial |
| Volume in Container | USP <697> | Meets USP requirements | Meets USP requirements | NP | NP |
| Sterility | USP <71> | Sterile | Pass | NP | NP |
| Endotoxins | USP <85> | NMT 4.0 EU/mL | Pass | NP | NP |

NMT = Not More Than;
NLT = Not Less Than;
RRT = Relative Retention Time;
NP = Not Performed;
ATM = Vendor Method Number

TABLE 3

Release and stability testing of 5-HTP for IV Infusion clinical batch at store at 5° C., horizontal position

| Testing | Method | Specification | Initial | 3 M | 6 M | 12 M |
|---|---|---|---|---|---|---|
| Appearance | ATM-1095 | Clear, light yellowish to green solution essentially free from visible particles | Clear, light yellowish solution, essentially free from visible particles | Clear, light yellowish solution, essentially free from visible particles | Clear, light yellowish solution, essentially free from visible particles | Clear, light yellowish solution, essentially free from visible particles |
| pH | USP<791> | 5.0-7.5 | 6.9 | 5.8 | 6.4 | 6.7 |
| Osmolality | USP<785> | NLT 250 mOsm | 318 mOsm | 305 mOsm | 304 mOsm | 306 mOsm |
| Assay | ATM-2135 | 90.0%-110.0% of label amount | Filtered: 101.8%<br>Unfiltered: 101.3% | Filtered: 101.8%<br>Unfiltered: 100.7% | Filtered: 101.0%<br>Unfiltered: 100.5% | Filtered: 99.8%<br>Unfiltered: 99.6% |
| Related Substances (% w/w) | ATM-2135 | Report Results Report Individual Related Substances ≥0.05% | Filtered<br>RRT 0.88: 0.05%<br>RRT 1.28: 0.05%<br>L-Tryptophan: 0.13%<br>Total: 0.23%<br>Unfiltered<br>RRT 1.28: 0.05%<br>L-Tryptophan: 0.12%<br>Total: 0.17% | Filtered<br>RRT 0.83: 0.07%<br>RRT 0.86: 0.16%<br>L-Tryptophan: 0.10%<br>Total: 0.33%<br>Unfiltered<br>RRT 0.83: 0.06%<br>RRT 0.86: 0.15%<br>RRT 1.62: 0.05%<br>L-Tryptophan: 0.10%<br>Total: 0.36% | Filtered<br>RRT 0.98: 0.07%<br>RRT 1.02: 0.05%<br>RRT 1.12: 0.25%<br>RRT 1.18: 0.09%<br>RRT 1.21: 0.12%<br>RRT 1.43: 0.07%<br>RRT 1.50: 0.10%<br>L-Tryptophan: 0.11%<br>Total: 0.86%<br>Unfiltered<br>RRT 0.98: 0.06%<br>RRT 1.12: 0.25%<br>RRT 1.18: 0.09%<br>RRT 1.21: 0.11%<br>RRT 1.43: 0.08%<br>RRT 1.50: 0.12%<br>L-Tryptophan: 0.11%<br>Total: 0.82% | Filtered<br>RRT 0.64: 0.05%<br>RRT 0.69: 0.05%<br>RRT 0.89: 0.35%<br>RRT 1.15: 0.07%<br>RRT 1.18: 0.18%<br>RRT 1.20: 0.07%<br>RRT 1.27: 0.08%<br>RRT 1.41: 0.07%<br>RRT 1.51: 0.19%<br>L-Tryptopban: 0.13%<br>Total: 1.2%<br>Unfiltered<br>RRT 0.64: 0.05%<br>RRT 0.69: 0.05%<br>RRT 0.89: 0.36%<br>RRT 1.15: 0.07%<br>RRT 1.18: 0.18%<br>RRT 1.20: 0.07%<br>RRT 1.27: 0.09%<br>RRT 1.41: 0.07%<br>RRT 1.51: 0.21%<br>L-Tryptopban: 0.12%<br>Total: 1.3% |
| Particulate Matter | USP <788> | Report Results | Filtered:<br>≥10 μm: 7 particles/vial<br>≥25 μm: 0 particles/vial<br>Unfiltered:<br>≥10 μm: 3347 particles/vial<br>≥25 μm: 153 particles/vial | Filtered:<br>≥10 μm: 193 particles/vial<br>≥25 μm: 27 particles/vial<br>Unfiltered:<br>≥10 μm: 24,893 particles/vial<br>≥25 μm: 660 particles/vial | Filtered:<br>≥10 μm: 93 particles/vial<br>≥25 μm:20 particles/vial<br>Unfiltered:<br>≥10 μm: 44,620 particles/vial<br>≥25 μm: 540 particles/vial | Filtered:<br>≥10 μm: 53 particles/vial<br>≥25 μm:0 particles/vial<br>Unfiltered:<br>≥10 μm: 161,247 particles/vial<br>≥25 μm: 587 particles/vial |

TABLE 3-continued

Release and stability testing of 5-HTP for IV Infusion clinical batch at store at 5° C., horizontal position

| Testing | Method | Specification | Initial | 3 M | 6 M | 12 M |
|---|---|---|---|---|---|---|
| Volume in Container | USP <697> | Meets USP requirements | Meets USP requirements | NP | NP | NP |
| Sterility | USP <71> | Sterile | No growth | NP | NP | NP |
| Endotoxins | USP <85> | NMT 4.0 EU/ml. | <0.05 EU/mL | NP | NP | NP |

NMT = Not More Than;
NLT = Not Less Than;
RRT = Relative Retention Time;
NP = Not Performed;
ATM = Vendor Method Example 3

Preparation of Drug Product for Administration in Humans—5-HTP Solution for IV Infusion Background: For human administration, the 5-HTP stock solution (5 mg per mL) was filtered and diluted with 0.9% sterile saline to a final concentration of about 0.07 mg/mL to 2.1 mg/mL in a total volume of 1000 mL. This final diluted product, intended for continuous IV infusion is referred to as "5-HTP solution for IV infusion".

Method: Generally, preparation of 5-HTP solution for IV infusion for human administration was performed using aseptic techniques in a biosafety cabinet or laminar flow hood under light-controlled conditions. After removal of the amber vial of 100 ml 5-HTP stock solution (5 mg/mL) from refrigerated storage, the contents were visually inspected and the appearance recorded. An appropriate amount of saline was drawn up in into a large volume syringe and transferred to an empty 1000 mL IV bag using a Luer connector. The 5-HTP stock solution was aspirated using a needle and syringe. The needle was removed and a sterile 0.22 μm filter was attached to the syringe. The contents of the syringe were ejected through the filter into the IV bag via the Luer connector. The IV bag was turned to mix.

More particularly, 5-HTP stock solution was diluted into IV bags to a final volume of 1000 mL with sterile saline according to the following calculations (based on body weight of subject):

Final 5-HTP concentration in IV bag (mg/mL)=(Dose level (X mg/kg)×Body Weight (Y kg))/1000 mL 5-HTP stock solution added to IV bag (mL)=(Final 5-HTP concentration in IV bag (mg/mL)/concentration of 5-HTP stock solution (mg/mL))×1000 ml 0.9% sterile saline added to IV bag (mL)=1000 mL—5-HTP for stock solution added to IV bag (mL)

Example 4

Stability of 5-HTP Solution for IV Infusion in IV Bags & Fluid Line

Background: To determine the stability of the 5-HTP solution for IV infusion in IV bags, (a) a short-term stability study was performed under refrigerated storage conditions, and (b) an in-use fluid line stability study was performed of the 5-HTP solution for IV infusion in IV bags when connected to an IV line, in a set up simulating the in-clinic IV infusion scenario. IV bags with 0.9% saline served as control.

Methods & Results:

Example 4a—Refrigeration Storage. For refrigeration storage stability, 5-HTP solution for IV infusion (2.1 mg/mL) was prepared as in Example 3, above, and stored at 5° C. for up to 48 hours in the dark. Samples were assessed for appearance (see Table 4, below), assay (see Table 5, below) and related substances. See Table 6, below. The results demonstrated that 5-HTP solution for IV infusion met acceptance criteria and were stable for at least up to 48 hours at 5° C.

Example 4b—Fluid line stability. For fluid line stability, 5-HTP solution for IV infusion 2.1 mg/mL was prepared as in Example 3, above, and passed through an entire IV infusion set over 24 hours at room temperature while protected from light. Samples were assessed for appearance (see Table 4, below), assay (see Table 5, below) and related substances (see Table 6, below). The results demonstrate that 5-HTP solution for IV infusion met acceptance criteria and were stable for at least 24 hours at 5° C. and for the duration of an exemplary infusion period, 24 hours, at room temperature, when shielded from light.

TABLE 4

Appearance of 5-HTP solution for IV infusion in IV bags & fluid line

| Condition | Sample Name | Sample Preparation | Condition | Acceptance Criteria | Time Point (hours) | | |
|---|---|---|---|---|---|---|---|
| | | | | | Initial | 24 | 48 |
| Refrigeration | 0.9% Saline, 1000 mL | | 5° C. | N/A | Clear, colorless solution free from visible particles | Clear, colorless solution free from visible particles | Clear, colorless solution free from visible particles |
| | 5-HTP solution for IV infusion 1000 mL | Preparation 1 Preparation 2 Preparation 3 | | Clear, light yellow solution free from visible particles | Clear, light yellow solution free from visible particles | Clear, light yellow solution free from visible particles | Clear, light yellow solution free from visible particles |

TABLE 4-continued

Appearance of 5-HTP solution for IV infusion in IV bags & fluid line

| Condition | Sample Name | Sample Preparation | Acceptance Condition | Acceptance Criteria | Time Point (hours) Initial | 24 | 48 |
|---|---|---|---|---|---|---|---|
| Fluid Line | 0.9% Saline, 1000 mL | | RT | N/A | ND | ND | ND |
| | 5-HTP solution for IV infusion 1000 mL | Preparation 1 Preparation 2 Preparation 3 | | Clear, light yellow solution free from visible particles | Clear, light yellow solution free from visible particles | Clear, light yellow solution free from visible particles | Clear, light yellow solution free from visible particles |

ND = Not Determined

TABLE 5

Assay of 5-HTP solution for IV infusion in IV bags & fluid line

| Condition | Sample Name | Sample Preparation | Condition | Acceptance Criteria | Initial | 24 | 48 |
|---|---|---|---|---|---|---|---|
| Refrigeration | 0.9% Saline, 1000 mL | | | N/A | ND | ND | ND |
| | 5-HTP solution for IV infusion 1000 mL | Preparation 1 Preparation 2 Preparation 3 | 5° C. | 90-110% of Label Claim | 101% 104% 100% | 94% 101% 104% | 94% 100% 100% |
| Fluid Line | 0.9% Saline, 1000 mL | | | N/A | ND | ND | ND |
| | 5-HTP solution for IV infusion 1000 mL | Preparation 1 Preparation 2 Preparation 3 | RT | 90-110% of Label Claim | 94% 101% 101% | 93% 100% 101% | 94% 100% 102% |

ND = Not Determined

TABLE 6

Related substances of 5-HTP solution for IV infusion in IV bags & fluid tine

| Condition | Sample Name | Sample Preparation | Condition | Acceptance Criteria | Initial | 24 | 48 |
|---|---|---|---|---|---|---|---|
| Refrigeration | 0.9% Saline, 1000 mL | | 5° C. | Report | ND | ND | ND |
| | 5-HTP solution for IV infusion 1000 mL | Preparation 1 | | | RRT 0.87: 0.07% L-Tryptophan: 0.13% Total: 0.20% | L-Tryptophan: 0.14% Total: 0.14% | RRT 0.87: 0.07% L-Tryptophan: 0.15% Total: 0.22% |
| | | Preparation 2 | | | RRT 0.87: 0.07% L-Tryptophan: 0.13% Total: 0.20% | RRT 0.88: 0.05% L-Tryptophan: 0.14% Total: 0.19% | RRT 0.87: 0.07% L-Tryptophan: 0.15% Total: 0.22% |
| | | Preparation 3 | | | RRT 087: 0.08% L-Tryptophan: 0.13% Total Imp: 0.21% | RRT 0.88: 0.05% L-Tryptophan: 0.18% Total Imp: 0.23% | RRT 0.88: 0.06% L-Tryptophan: 0.15% Total Imp: 0.21% |
| Fluid Line | 0.9% Saline, 1000 mL | | RT | Report | ND | ND | ND |
| | 5-HTP solution for IV infusion 1000 mL | Preparation 1 | | | RRT 0.87: 0.0734 L-Tryptophan: 0.15% Total Imp: 0.22% | RRT 0.87: 0.06% L-Tryptophan: 0.15% Total Imp: 0.21% | RRT 0.87: 0.06% L-Tryptophan: 0.15% Total Imp: 0.21% |
| | | Preparation 2 | | | RRT 0.87: 0.07% L-Tryptophan: 0.15% Total Imp: 0.22% | RRT 0.87: 0.06% L-Tryptophan: 0.15% Total Imp: 0.21% | RRT 0.87: 0.06% L-Tryptophan: 0.15% Total Imp: 0.20% |

TABLE 6-continued

Related substances of 5-HTP solution for IV infusion in IV bags & fluid tine

| Condition | Sample Name | Sample Preparation | Sample Condition | Acceptance Criteria | Time Point (hours) | | |
|---|---|---|---|---|---|---|---|
| | | | | | Initial | 24 | 48 |
| | | Preparation 3 | | | RRT 0.87: 0.07% L-Tryptophan: 0.15% Total Imp: 0.22% | RRT 0.87: 0.06% L-Tryptophan: 0.15% Total Imp: 0.20% | RRT 0.87: 0.06% L-Tryptophan: 0.15% Total Imp: 0.21% |

RRT: Relative Retention Time;
ND

Example 5

Administration and Pharmacokinetics of a Continuous IV 5-HTP Infusion in Healthy Subjects Methods:

Study Design. A Phase 1, randomized, double-blind, placebo-controlled, single ascending dose study was performed to evaluate the safety, tolerability and pharmacokinetics (PK) of 5-HTP solution for IV infusion when administered to healthy adults taking a selective serotonin reuptake inhibitor (SSRI), escitalopram, for 3 weeks. Study duration was 37±3 days. The total individual subject participation time was no more than 66 days including screening, dosing, and follow-up phases. The IV infusion duration was 24 h, dosing with 5-HTP solution for IV infusion (see Example 3, above) or placebo (0.9% saline).

Subjects. A total of 39 healthy male and female subjects were randomized across 5 cohorts, each with 8 subjects (6 active:2 placebo) per cohort except for Cohort 5 (5 active:2 placebo). For each cohort, first 2 sentinel subjects received IV 5-HTP (N=1) or placebo (N=1) prior to dosing of the remaining 5 or 6 subjects.

Pre-treatment with escitalopram. All subjects received pretreatment with escitalopram for 3 weeks prior to and during the 24 h IV infusion. A supply of escitalopram was provided for self-administration at a dose of 10 mg/day for 7 days. On Day 7 subjects were evaluated for general health and tolerability of escitalopram. Escitalopram compliance confirmation was evaluated by taking a blood draw for escitalopram plasma level measurements and by monitoring pill count using a diary. On Day 7 the subjects received a supply of 20 mg escitalopram tablets and self-administered 20 mg/day until Day 20 when they were admitted to the impatient clinic. Escitalopram was co-administered orally on Day 21-23 by clinical staff. Escitalopram treatment was tapered from 20 mg/day to 10 mg/day after the end of the infusion and continued for 8 days.

IV infusion. 5-HTP solution for IV infusion or placebo was administered IV at a constant rate or ramped rate of infusion over 24 hr.

Constant rate infusion. 5-HTP solution for IV infusion was administered at constant infusion rates of 1 mg/kg/24 hr in Cohort 1 and 3 mg/kg/24 hr in Cohort 2. The infusion rate was 41.67 ml/h.

Ramp rate infusion. To gradually elevate 5-HTP plasma levels, 5-HTP solution for IV infusion was administered at a ramp rate of infusion for Cohorts 3, Cohort 4, and Cohort 5, at average 5-HTP infusion rates of 3 mg/kg/24 hr, 2 mg/kg/24 hr and 1 mg/kg/24 hr, respectively. The infusion volume rates were 13.89 ml/hr at T=0-4 hr; 27.78 ml/hr at T=4-8 hr; 41.67 ml/hr at T=8-12 hr; and 55.55 ml/hr at T=12-24 hr.

Bioanalysis. Plasma samples for 5-HTP analysis were collected and stored at −80° C. Plasma samples for escitalopram analysis were collected and stored at −80° C. Plasma 5-HTP levels and plasma escitalopram levels were measured using standard liquid chromatography with tandem mass spectrometry (LC-MS-MS) methods. For 5-HTP analysis, plasma samples were collected at T=0, 1, 2, 3, 4, 5, 6, 8, 10, 12, 14, 22, 24, 26, 28, 30, 32, 36, and 48 hr. For escitalopram analysis, plasma samples were collected on Day 7, Day 21 (pre-infusion), Day 22 (end of infusion), and Day 23 (24 hr after end of infusion). Plasma escitalopram levels were averaged across days 21-23, during the time-period when subjects were admitted to the clinic and received 5-HTP solution for IV infusion or placebo.

Statistical analysis. Subjects receiving placebo across the 5 cohorts (N=2 per cohort) were pooled. Descriptive statistics were calculated for each quantitative variable within each treatment group and placebo (n, mean, standard deviation, median, minimum, maximum).

PK analysis of plasma escitalopram. Plasma escitalopram levels across Days 21-23 were averaged for each subject, and statistical analysis by one-way ANOVA for cohort differences executed using GraphPad Prism version 9.4.1.

PK analysis of plasma 5-HTP. The PK population included subjects who received 5-HTP solution for IV infusion and completed the 24 h infusion. PK parameters were computed for each Cohort/dose/infusion paradigm. Placebo data from all cohorts were pooled. The following PK parameters were computed: $C_{Max}$, $T_{Max}$, AUC 0-infinity ($AUC_{Inf}$), AUC 0-36 h ($AUC_{36\ h}$), AUC 0-48 h ($AUC_{48\ h}$), AUC 0-last ($AUC_{Last}$), and $T_{1/2}$. PK parameters were computed by non-compartmental analysis from the concentration-time data using WinNonlin version 8.3, unless noted Results:

Plasma escitalopram. Plasma escitalopram levels averaged across Days 21-23 for each of the 5 active treatment groups and placebo treatment group are presented in Table 7, below. The average plasma escitalopram levels ranged from 24-44 ng/mL, which is within the therapeutic range (Rao, 2007). There were no significant differences in average escitalopram levels between treatment groups.

Plasma 5-HTP. Plasma 5-HTP PK parameters for each treatment group are presented in Table 8 below.

Constant rate infusion. Cohorts 1 and 2 were administered 5-HTP solution for IV infusion at 1 mg/kg/24 hr and 3 mg/kg/24 hr, respectively, using a constant flow rate. In Cohort 2, receiving 3 mg/kg/24 hr 5-HTP solution for IV infusion, 2 subjects discontinued treatment after 1.5 and 5.5 hours of infusion, respectively, due to mild, but intolerable adverse events. (See Example 6, below, for adverse events). The 2 discontinued subjects were excluded from the PK analysis. The 2 discontinued subjects had higher initial 5-HTP plasma levels (T=1 h: 248 and 304 ng/ml) compared to the 4 subjects completing the infusion (T=1 h: 163, 243, 109, and 217 ng/ml). Therefore, the PK data from Cohort 2, 3 mg/kg/24 hr 5-HTP solution for IV infusion, may be moderately confounded, underestimating the average exposure produced across subjects in Cohort 2. Average steady state plasma levels were achieved approximately 4 h after the start of infusion for both 1 mg/kg/24 hr and for 3 mg/kg/24 hr constant 5-HTP infusion rates and remained stable for the duration of the infusion. See FIG. 1. Due to a flush of the IV bag/fluid line around 22 h—to ensure the entire 1000 ml volume of 5-HTP solution for IV infusion was administered to the subject—a moderate flow increase followed by a flow decrease skewed the 22 h time point 5-HTP plasma levels high and the 24 h time point plasma 5-HTP levels low. This artefact did not affect the $C_{Ave}$ and AUC values.

Figure 2:
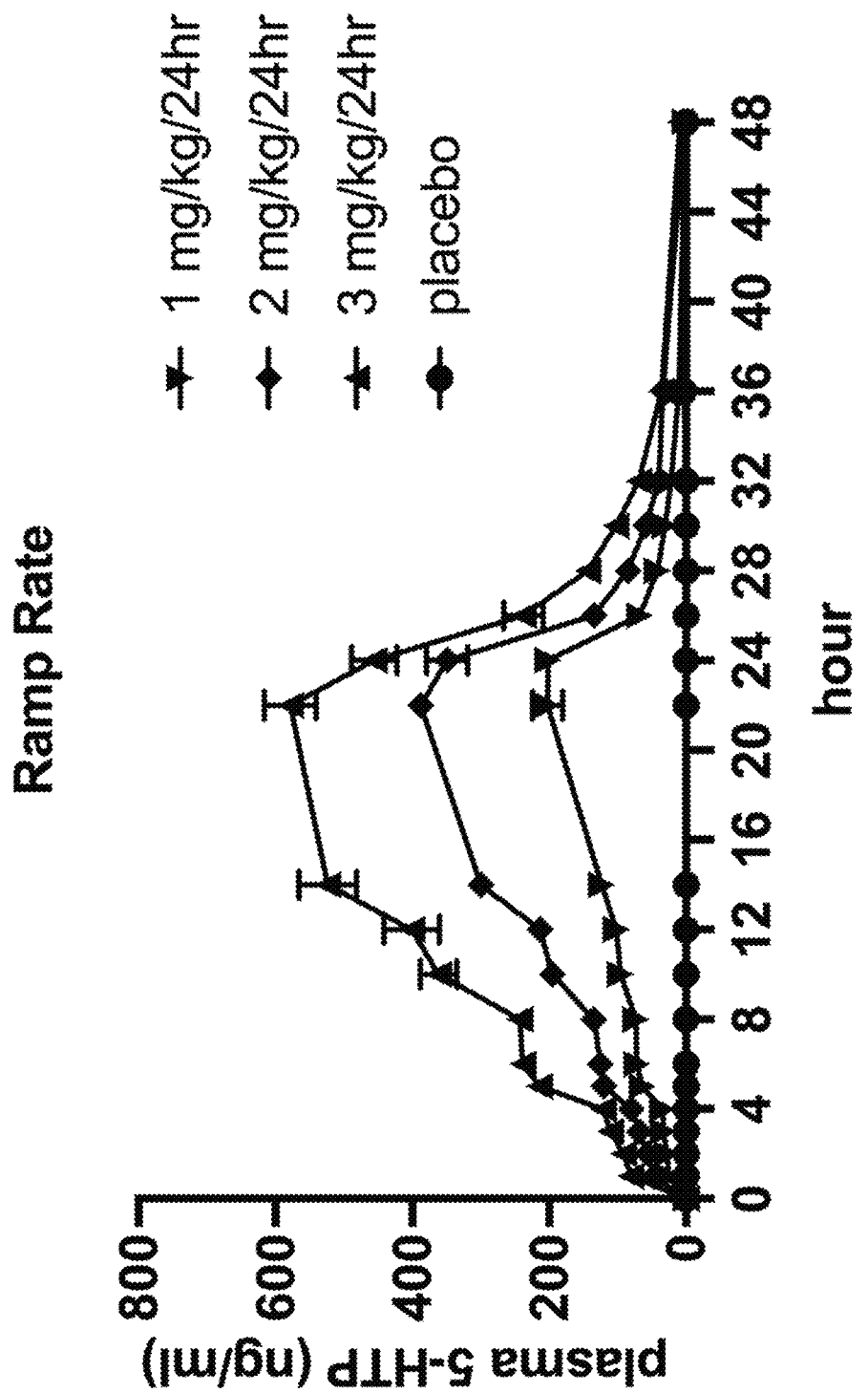
FIG. 2 is a graph showing plasma 5-hydroxytryptophan (5-HTP) concentration (nanograms per milliliter (ng/ml)) versus time profiles of ascending average 5-HTP infusion rates for continuous intravenous (IV) infusion using a variable 5-HTP infusion rate and a ramp flow rate (i.e., a variable infusion volume rate) across 24 hours. Data for an average 5-HTP infusion rate of 1 milligram per kilogram per day (mg/kg/24 hr), i.e., "1 mg/kg/24 hr" is shown in downward-pointing triangles; data for an average 5-HTP infusion rate of 2 mg/kg/24 hr, i.e., "2 mg/kg/24 hr" is shown in diamonds; data for an average 5-HTP infusion rate of 3 mg/kg/24 hr, i.e., "3 mg/kg" is shown in upward-pointing triangles; and data for a placebo is shown in circles. Data shown are means f SEM.

Ramp rate infusion. Average steady state plasma levels were achieved between 14-24 h for the three variable 5-HTP infusion rate profiles at an average rate of 1-, 2-, and 3 mg/kg/24 hr. See FIG. 2. The moderate artefact caused by the flush of IV bag/fluid line skewed the 22 h and 24 h 5-HTP plasma levels similarly in Cohorts 3-5, compared to what observed in Cohorts 1 and 2.

Comparison of 5-HTP PK parameters between constant and ramped flow infusion. There were no significant differences in $C_{Ave}$, $AUC_{Inf}$ or $AUC_{Last}$ between constant rate and ramp rate infusion at 1 mg/kg/24 hr or 3 mg/kg/24 hr average infusion rates (p>0.05, unpaired t-test. GraphPad Prism version 9.4.1.).

Example 6

Dose-Proportionality Assessment of IV 5-HTP Continuous Infusion

Background: The term dose proportionality denotes a proportional and linear relationship between dose and a pharmacokinetic measure, for the specific (i) dose-range, (i) dosing route, and (iii) dosing regimen investigated. More particularly, if doubling the dose doubles the pharmacokinetic measure of maximal ($C_{Max}$) or total (AUC) systemic exposure to the compound administered, then dose proportionality is present, at least within the dose ranges examined. Hence, if dose proportionality is met, a plot of dose vs pharmacokinetic measure produces a straight line, with obviously a constant slope, within the specific (i) dose-range, (i) dosing route, and (iii) dosing regimen investigated. The relationship between dose and plasma compound concentration (C (e.g., $C_{Max}$ or AUC)) can be described via the following equation:

$$C = \alpha \, dose^{\beta}$$

When $\beta=1$, dose proportionality is present. If so, $C=\alpha$ dose. $\alpha$ is a constant relating dose to C, for a given range of C and given dose units, and is identical to the slope of the regression line. In the power model (Smith et al, 2000), dose proportionality is assessed via the following linear equation:

$$\log(C) = \log(\alpha) + \beta \times \log(dose) + error$$

Based on standard statistical methods for linear models, estimates for $\beta$ together with confidence limits can be derived. In practical terms, dose proportionality is generally

TABLE 7

Plasma escitalopram levels

| Cohort | 5-HTP dose (mg/kg) | Infusion scheme | N | Escitalopram plasma levels (ng/ml) | | | | |
|---|---|---|---|---|---|---|---|---|
| | | | | Day 7 | Day 21 | Day 22 | Day 23 | Average Day 21-23 |
| 1 | 1 | Constant | 6 | 19.3 ± 3.1 | 39.8 ± 12.3 | 37.9 ± 7.3 | 41.6 ± 7.6 | 39.7 ± 8.9 |
| 2 | 3 | Constant | | 10.1 ± 1.5 | 22.5 ± 10.2 | 24.3 ± 5.7 | 30.0 ± 3.7 | 25.6 ± 6.5 |
| 3 | 3 | Ramped | 6 | 17.0 ± 2.3 | 43.5 ± 4.5 | 37.3 ± 5.9 | 36.6 ± 4.1 | 39.1 ± 4.8 |
| 4 | 2 | Ramped | 6 | 14.2 ± 2.5 | 28.5 ± 5.8 | 28.8 ± 6.2 | 30.3 ± 7.0 | 29.2 ± 6.2 |
| 5 | 1 | Ramped | | 11.4 ± 2.3 | 21.7 ± 3.4 | 22.2 ± 4.7 | 29.2 ± 7.5 | 24.4 ± 5.0 |
| 1-5 | placebo | Constant/ramped | 10* | 18.3 ± 3.1 | 43.3 ± 8.4 | 45.2 ± 9.1 | 43.5 ± 7.5 | 44.0 ± 8.2 |

Data are arithmetic mean ± SEM.
*Placebo data is pooled, N = 2/cohort.

TABLE 8

Plasma 5-HTP Pharmacokinetics Across Treatments

| Cohort | 5-HTP dose (mg/kg) | Flow Rate* | $C_{Ave}$ (0-24 h) (ng/ml) | $C_{Max}$ (ng/ml) | $T_{1/2}$ (h) | $AUC_{Last}$ (h*ng/ml) | $AUC_{Inf}$ h*ng/ml |
|---|---|---|---|---|---|---|---|
| 1 | 1 | constant | 94 | 140.8 | 3.71 | 2914 | 2970 |
| 2 | 3 | constant | 268 | 427.3 | 4.84 | 8797 | 8854 |
| 3 | 3 | ramp | 264 | 592.0 | 5.1 | 10886 | 10950 |
| 4 | 2 | ramp | 160 | 394.7 | 4.4 | 6332 | 6435 |
| 5 | 1 | ramp | 82 | 208.8 | 4.52 | 3238 | 3291 |
| placebo | 0 | both | 0 | 3.8 | 0 | 76 | 0 |

*Constant flow rate-41.67 ml/h. Ramp flow rate-0-4 h: 13.89 mL/h; 4-8 h: 27.78 ml/h; 8-12 h: 41.67 ml/h; 12-24 h 55.55 ml/h. Cave, Cmax, $t_{1/2}$ and AUC are arithmetic mean values. N = 6 for Cohorts 1, 3 and 4, N = 4 for Cohort 2, N = 5 for Cohort 5, N = 10 for placebo (N = 2/Cohort).

accepted if β~1 and the 90% confidence limits are between 0.8 and 1.25 (Smith et al, 2000).

Methods: Applying the approach by Smith (Smith et al, 2000), using a general linear model and SAS software Version 9.4, dose proportionality of continuously administered IV 5-HTP was assessed using the data in Table 9, below. Only data from ramped rate 1 mg/kg/24 hr, 2 mg/kg/24 hr, and 3 mg/kg/24 hr were used, as 3 dose levels of the compound administered the same way are generally required for modelling dose proportionality.

TABLE 9

Individual subject PK data.

| Subject Number | Treatment | $C_{Max}$ (ng/mL) | $AUC_{Last}$ (h · ng/mL) | $AUC_{Inf}$ (h · ng/mL) |
|---|---|---|---|---|
| 01-016 | Constant rate 1 mg/kg/24 hr | 189 | 3762.18 | 3832.68 |
| 01-024 | Constant rate 1 mg/kg/24 hr | 114 | 2185.63 | 2234.41 |
| 01-031 | Constant rate 1 mg/kg/24 hr | 169 | 3291.36 | 3351.07 |
| 01-033 | Constant rate 1 mg/kg/24 hr | 118 | 2831.00 | 2922.39 |
| 01-034 | Constant rate 1 mg/kg/24 hr | 112 | 2530.16 | 2551.36 |
| 01-038 | Constant rate 1 mg/kg/24 hr | 143 | 2885.80 | 2930.09 |
| 01-029 | Constant rate 3 mg/kg/24 hr | 397 | 7959.93 | 7998.37 |
| 01-050 | Constant rate 3 mg/kg/24 hr | 480 | 9690.71 | 9781.13 |
| 01-051 | Constant rate 3 mg/kg/24 hr | 320 | 6999.32 | 7039.23 |
| 01-053 | Constant rate 3 mg/kg/24 hr | 512 | 10537.75 | 10597.49 |
| 01-056 | Ramp rate 3 mg/kg/24 hr | 613 | 11118.86 | 11154.80 |
| 01-064 | Ramp rate 3 mg/kg/24 hr | 660 | 11310.89 | 11393.96 |
| 01-066 | Ramp rate 3 mg/kg/24 hr | 679 | 13698.51 | 13786.66 |
| 01-068 | Ramp rate 3 mg/kg/24 hr | 644 | 10738.77 | 10786.90 |
| 01-070 | Ramp rate 3 mg/kg/24 hr | 454 | 8350.62 | 8427.71 |
| 01-074 | Ramp rate 3 mg/kg/24 hr | 502 | 10098.28 | 10152.61 |
| 01-077 | Ramp rate 2 mg/kg/24 hr | 407 | 6538.74 | 6653.62 |
| 01-082 | Ramp rate 2 mg/kg/24 hr | 373 | 6191.76 | 6254.18 |
| 01-089 | Ramp rate 2 mg/kg/24 hr | 352 | 6095.21 | 6207.11 |
| 01-090 | Ramp rate 2 mg/kg/24 hr | 385 | 6245.16 | 6316.80 |
| 01-093 | Ramp rate 2 mg/kg/24 hr | 414 | 5955.75 | 6043.68 |
| 01-096 | Ramp rate 2 mg/kg/24 hr | 437 | 6968.01 | 7134.20 |
| 01-103 | Ramp rate 1 mg/kg/24 hr | 179 | 2771.73 | 2813.29 |
| 01-105 | Ramp rate 1 mg/kg/24 hr | 266 | 4345.10 | 4399.83 |
| 01-115 | Ramp rate 1 mg/kg/24 hr | 247 | 3799.02 | 3862.84 |
| 01-121 | Ramp rate 1 mg/kg/24 hr | 192 | 2767.78 | 2807.47 |
| 01-123 | Ramp rate 1 mg/kg/24 hr | 160 | 2505.93 | 2572.27 |

Results & Discussion: The computational output according to the approach by Smith (Smith et al, 2000) is shown in Table 10, below. For all three PK parameters, the estimates for β were close to 1. For $AUC_{Last}$ and $AUC_{Inf}$, but not for $C_{Max}$, the 90% upper confidence limits slightly exceeded the conventional 1.25 limit; however, this appeared to be attributable to the low N (5-6 subjects per group), as also reflected in the relatively high standard error. Hence, dose proportionality for doses up to 3 mg/kg/24 hr was accepted. While the data used to assess dose proportionality derived from the ramped rate infusion, dose-proportionality can also be assumed for other continuous infusions, provided the $C_{Max}$ is equal or below about 592 ng/ml, the average $C_{Max}$ recorded for 3 mg/kg/24 hr ramped rate.

TABLE 10

Dose-proportionality

| PK parameter | Estimate β | Standard Error | 90% confidence limits | |
|---|---|---|---|---|
| | | | 0.8 | 1.25 |
| $C_{Max}$ | 0.954717237 | 0.08416149 | 0.807177907 | 1.102256567 |
| $AUC_{Last}$ | 1.105973465 | 0.08897322 | 0.949998934 | 1.261947997 |
| $AUC_{Inf}$ | 1.096705713 | 0.08799864 | 0.942439671 | 1.250971756 |

Example 7

Dose-Exposure Relationship Between IV 5-HTP Continuous Infusion and 5-HTP Plasma Levels Background: Having established dose proportionality, the relationship between the 5-HTP IV infusion dosed continuously and 5-HTP plasma exposure was examined. As dose proportionality was established, simple linear regression can describe the relationship between the 5-HTP IV infusion dose (i.e., the average 5-HTP infusion rate) and 5-HTP exposure. Having established that endogenous plasma 5-HTP is negligible, compared to the 5-HTP exposure caused by the 5-HTP IV infusion (see Table 8, above), it is justified to force the regression line through the origin (X=0, Y=0). Hence, AUC=α×IV 5-HTP dose (mg/kg/24 hr), where α is the slope.

Method: To determine the slope in the equation AUC=α× IV 5-HTP dose (mg/kg/24 hr) linear regression using Prism Version 9.4.0 was performed, forcing the line through the origin, using the $AUC_{Last}$ and $AUC_{Inf}$ data from the ramp rate groups, i.e., 1 mg/kg/24 hr, 2 mg/kg/24 hr, and 3 mg/kg/24 hr. See FIG. 2. Additionally, linear regression was performed on $AUC_{Last}$ and $AUC_{Inf}$ data from each treatment group individually. See Table 10, below.

Results & discussion: The equation for $AUC_{Last}$ was:

$$AUC_{Last}=3471 \text{ (95\% confidence limits: 3197 to } 3746) \times \text{IV 5-HTP dose (mg/kg/24 hr)}$$

The equation for $AUC_{Inf}$ was:

$$AUC_{Inf}=3503 \text{ 95\% confidence limits: 3231 to } 3776) \times \text{5-HTP IV dose (mg/kg/24 hr)}$$

Figure 3B:
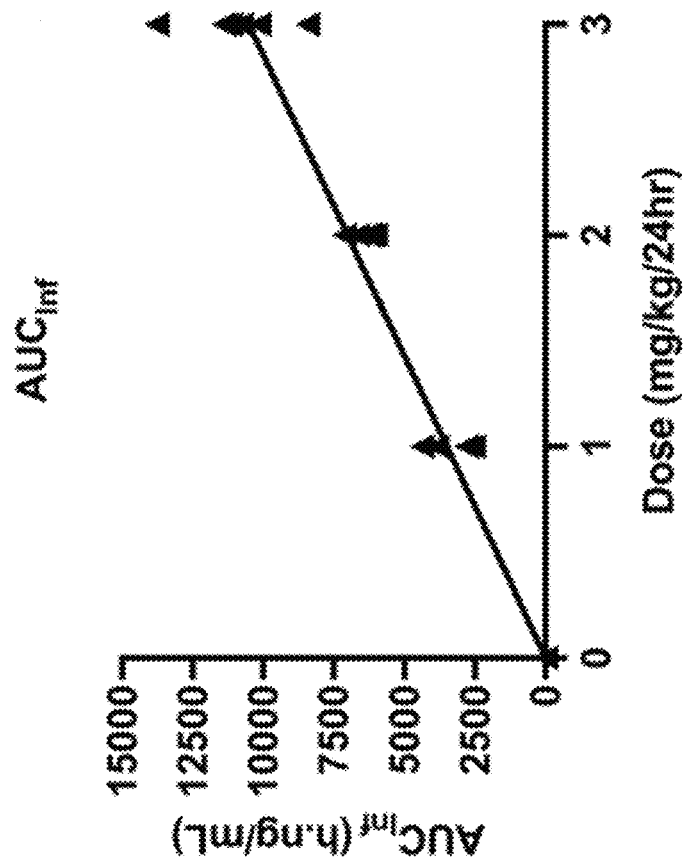
FIG. 3B is a graph showing the linear regression of area under the concentration-time curve extrapolated to infinity (AUC$_{Inf}$; expressed in hours times nanograms per milliliter (h·ng/ml)) versus average 5-hydroxytryptophan (5-HTP) infusion rate (in milligram per kilogram per day (mg/kg/24 hr)) using data from continuous intravenous (IV) infusion 5-HTP with ramp flow rates (i.e., variable infusion volume rates) and average 5-HTP infusion rates of 1 mg/kg/24 hr, 2 mg/kg/24 hr, and 3 mg/kg/24 hr.
Figure 3A:
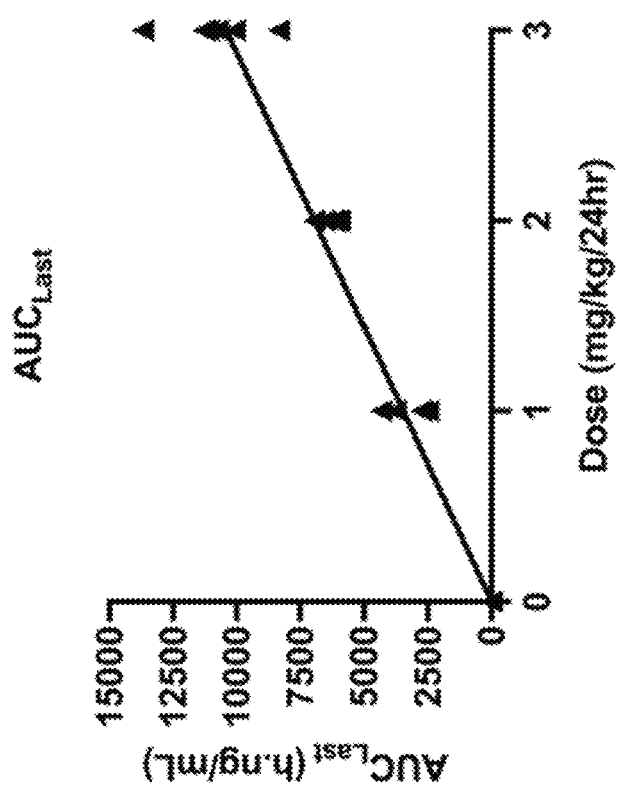
FIG. 3A is a graph showing the linear regression of area under the concentration-time curve to the last measured concentration (AUC$_{Last}$; expressed in hours times nanograms per milliliter (h·ng/ml)) versus average 5-hydroxytryptophan (5-HTP) infusion rate (in milligram per kilogram per day (or per 24 hours; mg/kg/24 hr)) using data from continuous intravenous (IV) infusion 5-HTP using a ramp flow rate (i.e., a variable infusion volume rate) with average 5-HTP infusion rates of 1 mg/kg/24 hr, 2 mg/kg/24 hr, and 3 mg/kg/24 hr.

FIGS. 3A and 3B show the linear regression lines and 95% confidence limits. The α for $AUC_{Last}$ and $AUC_{Inf}$ were essentially identical, reflecting that at $T_{Last}$, the 5-HTP plasma had returned essentially to baseline. See FIG. 2. The linear regression a determined from each treatment group individually did not differ statistically. See Table 11, below. The data support that 5-HTP plasma exposure, i.e., $AUC_{Inf}$, resulting from a continuous infusion of IV 5-HTP can be predicted from the equation $AUC_{Inf}$=3500×(mg/kg). At least up to 3 mg/kg, a $C_{Av0-24 h}$ about 264 ng/ml, and a $C_{Max}$ of about 592 ng/ml, dose and infusion regimen did not meaningfully impact the α of the equation AUC=α×IV 5-HTP dose (mg/kg).

TABLE 11

Dose-exposure relationship linear regression on individual treatment groups

| | $AUC_{Last}$ | | $AUC_{Inf}$ | |
|---|---|---|---|---|
| Treatment | Mean slope | 95% confidence limits | Mean slope | 95% confidence limits |
| Constant rate 1 mg/kg/24 hr | 2914 | 2331 to 3498 | 2970 | 2375 to 3566 |
| Constant rate 3 mg/kg/24 hr* | 2932 | 2079 to 3785 | 2951 | 2089 to 3813 |
| Ramp rate 1 mg/kg/24 hr | 3238 | 2253 to 4222 | 3291 | 2303 to 4280 |
| Ramp rate 2 mg/kg/24 hr | 3176 | 2975 to 3376 | 3196 | 2930 to 3461 |
| Ramp rate 3 mg/kg/24 hr | 3629 | 3018 to 4239 | 3650 | 3038 to 4262 |

*Data potentially underestimate AUCs as two subjects dropped out.

Example 8

Safety and Tolerability of IV 5-HTP Continuous Infusion

Methods: Safety and tolerability of the IV 5-HTP continuous infusion were assessed during the 24 hr administration of IV 5-HTP infusion (see Example 5) or placebo and approximately 24 hr after end of the infusion. Safety and tolerability of the IV 5-HTP infusion were assessed by monitoring of adverse events (AEs), standard clinical safety laboratory tests, electrocardiograms (ECG), vital signs, and clinical scales of suicidality. The safety population included all subjects. Vital sign measurements included systolic blood pressure (mmHg), diastolic blood pressure (mmHg), heart rate (beats/min), respiratory rate (breaths/min), and oral temperature. Twelve-lead electrocardiogram measurements were performed in triplicate. The recorded parameters included heart rate (beats/min), PR (msec), QRS (msec), and QTcF (msec). Assessments were rated as normal, not clinically significant, or clinically significant. Clinical laboratory tests included a complete blood count, chemistry panel, coagulation panel, and thyroid stimulating hormone.

Statistics: Descriptive statistics (n, mean, SD, minimum, and maximum) for absolute values and changes from baseline were calculated.

Results: There were no safety findings reported for clinical safety laboratory tests, vital signs, or 12-lead electrocardiograms that were associated with the IV 5-HTP infusion.

Adverse events (AEs) deemed related to IV 5-HTP were primarily gastrointestinal in nature and included nausea, vomiting, and diarrhea, consistent with a 5-HT mechanism. Other mild AEs reported included: nervous system disorders including dizziness (N=1 at 2 mg/kg/24 hr ramp rate infusion), and mild serotonin toxicity (N=1) at 3 mg/kg/24 hr constant rate infusion; general disorders including chills (N=1 at 2 mg/kg/24 hr ramp rate infusion) and feeling hot (N=1 at 2 mg/kg/24 hr ramp rate infusion); and skin and subcutaneous disorders including rash (N=1 at 2 mg/kg/24 h ramp rate infusion). All AEs were mild-to-moderate severity. The incidence of AEs was more commonly associated with higher IV 5-HTP doses and 5-HTP plasma exposure>100 ng/ml. No serious or severe AEs related to the IV 5-HTP infusion were observed in any subjects. The number and percent of subjects with adverse events related to poor tolerability of the IV 5-HTP infusion (e.g., gastrointestinal disorders and serotonin toxicity) reported within each cohort are presented in Table 12, below. The incidence of AEs was generally dose dependent. The incidence of AEs was dependent on the type of flow rate of infusion.

Constant rate infusion: At constant flow rate IV 5-HTP infusion there were no AEs in the 1 mg/kg/24 hr group. In contrast, AEs of mild severity were recorded for all subjects in the 3 mg/kg/24 hr at constant rate infusion. These AEs included nausea (6/6), vomiting (5/6) and diarrhea (1/6). A constant infusion rate of 5-HTP IV infusion at a dose of 3 mg/kg/24 hr resulted in discontinued treatment after 1.5 hours in one subject and at 5.5 hours of infusion in another subject due to mild adverse events. The subject stopping the 5-HTP IV infusion after 5.5 hours was diagnosed with mild serotonin toxicity, which rapidly resolved after stopping the infusion. The rapid increase in plasma 5-HTP levels (250-300 ng/ml within 1 h) in these subjects was likely a causal factor contributing to the onset of tolerability issues that resulted in discontinuing the infusion of IV 5-HTP at a dose of 3 mg/kg/24 hr at a constant flow rate.

Ramp rate infusion: AEs of mild-to-moderate severity were observed in cohorts receiving ramp flow rate IV 5-HTP infusion. The incidence of AEs at the ramp flow rate was generally dose dependent. At a dose of 1 mg/kg/24 hr mild AEs included nausea (1/5) and vomiting (1/5) and moderate AEs included nausea (1/5) and vomiting (1/5). At a dose of 2 mg/kg/24 hr mild AEs included nausea (4/6), vomiting (4/6), and diarrhea (4/6), chills (1/6) and dizziness (1/6). At a dose of 3 mg/kg/24 hr mild AEs included nausea (3/6) and vomiting (2/6), and diarrhea (1/6). While there were no AEs at the 1 mg/kg/24 hr dose using constant infusion, AEs occurred in 2 subjects receiving a 1 mg/kg/24 hr dose using a ramp flow rate infusion. It is noteworthy that the AEs that occurred using the ramp flow rate 1 mg/kg/24 hr IV 5-HTP infusion did not manifest until the highest flow rate of 55.55 ml/h was reached, associated with 5-HTP plasma levels from 112-266 ng/mL.

Comparison of AEs between flow rate scheme at the same dose levels of 5-HTP IV infusions: At a dose of 1 mg/kg/24 hr, there were no AEs using a constant rate of infusion. In contrast, mild and moderate AEs were observed using a ramp rate of infusion. At a dose of 3 mg/kg/24 hr there were fewer AEs observed using a ramp rate of infusion compared to a constant rate of infusion. Thus, a constant flow rate of infusion appears to be better tolerated than the ramp flow rate at a 1 mg/kg/24 hr dose, which could be due to that $C_{Max}$ was higher for the ramped infusion. Conversely, a ramp flow rate infusion appears to be better tolerated than the constant flow rate at a 3 mg/kg/24 hr dose, which could be because the constant flow rate produced a very rapid $T_{Max}$, i.e., early high 5-HTP plasma levels.

TABLE 12

Selected adverse events[1] from the continuous IV 5-HTP by dose and infusion flow rate.

| Cohort | Dose (mg/kg/24hr) | Infusion Rate | Nausea n/N (%) | Vomiting n/N (%) | Diarrhea n/N (%) | Serotonin Toxicity n/N (%) |
| --- | --- | --- | --- | --- | --- | --- |
| Cohort 1 | 1 | Constant | 0/6 (0.0) | 0/6 (0.0) | 0/6 (0.0) | 0/6 (0.0) |
| Cohort 2 | 3 | Constant | 6/6 (100.0) | 6/6 (100.0) | 1/6 (16.7) | 1/6 (16.7) |
| Cohort 3 | 3 | Ramp | 4/6 (66.7) | 2/6 (33.3) | 1/6 (16.7) | 0/6 (0.0) |
| Cohort 4 | 2 | Ramp | 4/6 (66.7) | 4/6 (66.7) | 4/6 (66.7) | 0/6 (0.0) |
| Cohort 5 | 1 | Ramp | 2/5 (40.0) | 2/5 (40.0) | 0/5 (0.0) | 0/5 (0.0) |
| Cohort 1-2 | placebo | Constant | 0/4 (0.0) | 0/4 (0.0) | 0/4 (0.0) | 0/4 (0.0) |
| Cohort 3-5 | | Ramp | 0/6 (0.0) | 0/6 (0.0) | 0/6 (0.0) | 0/6 (0.0) |

[1]Adverse events include gastrointestinal events and serotonin toxicity only. For other adverse events see Example 8.
N: Number of subjects within the cohort dosed with respective treatment; n: number of subjects with adverse event.

Example 9

Pharmacodynamics of IV 5-HTP—Acute Increase in Plasma Cortisol

Background: Compounds that acutely elevate brain 5-$HT_{Ext}$ can activate the hypothalamic pituitary adrenal axis and induce the release of cortisol from the adrenals into the plasma (Attenburrow et al, 2001; Demisch et al, 1986; Guan et al, 2020; Kapitany et al, 1999; Lowe et al, 2006; Meltzer et al, 1983; Sargent et al, 1998). Generally large, acute increases in brain 5-$HT_{Ext}$ are required to increase cortisol and the effect desensitizes rapidly with prolonged serotonin elevation (Mashchak et al, 1983). A cortisol plasma increase is thus a simple assay to demonstrate target engagement, i.e., that 5-HTP reaches the brain and increases 5-$HT_{Ext}$—in this study increases 5-$HT_{Ext}$ beyond the effect of serotonin reuptake inhibitor therapy, as the subjects were treated with the SSRI escitalopram.

Method: Total plasma cortisol levels (expressed in μg/dL) were quantified using standard immunoassay methodology. Total plasma cortisol levels were measured at multiple time points during the 24 hr infusion period of 5-HTP solution for IV infusion or placebo. Total plasma cortisol levels were measured at baseline (T=0) before the start of infusion. Blood samples were collected at T=0, and at pre-specified timepoints following initiation of infusion (2, 4, 6, 8, 10, 12, 14, 22, 24 hr). The pharmacodynamic population included subjects who received IV 5-HTP and completed the 24 h infusion or placebo and who had escitalopram levels above the lower limit of quantitation.

Figure 4B:
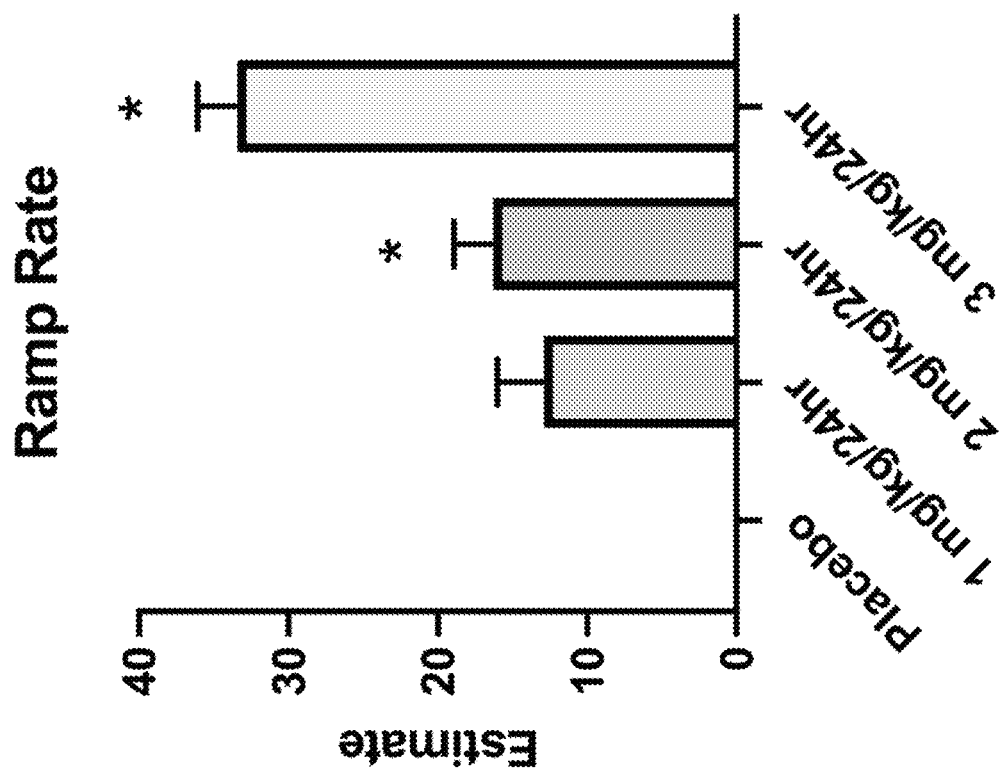
FIG. 4B is a graph showing the estimated increase in plasma cortisol levels relative to placebo at 14 hours for variable infusion rate intravenous (IV) infusion of 5-hydroxytryptophan (5-HTP) at an average 5-HTP infusion rate of 1 milligram per kilogram per day (mg/kg/24 hr), 2 mg/kg/24 hr, or 3 mg/kg/24 hr, referred to as "1 mg/kg/24 hr", "2 mg/kg/24 hr", and "3 mg/kg/24 hr" on the bottom of the graph. Data shown are means±SEM.
Figure 4A:
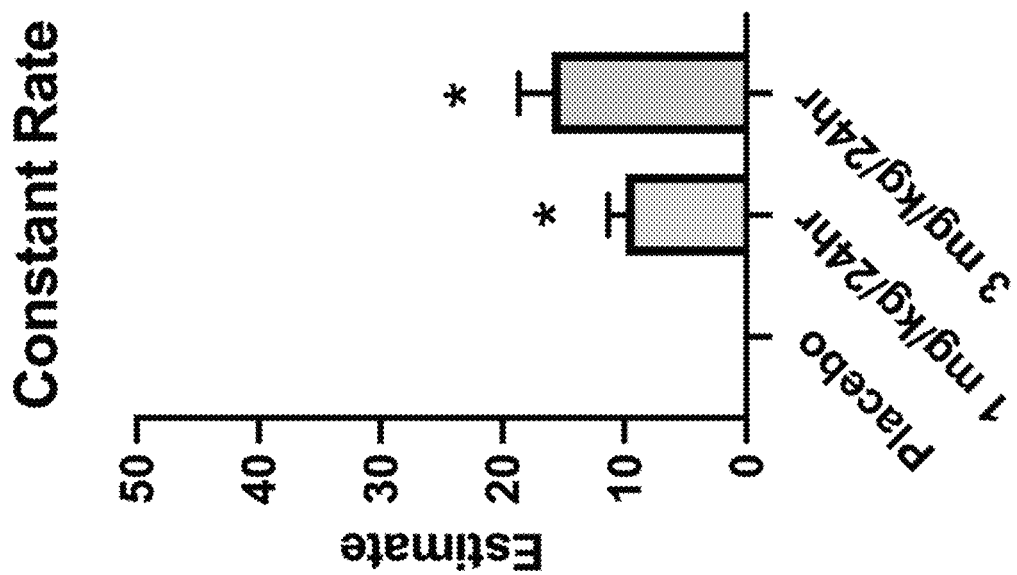
FIG. 4A is a graph showing the estimated increase in plasma cortisol levels relative to placebo at 2 hours for intravenous (IV) infusion of 5-hydroxytryptophan (5-HTP) at a constant 5-HTP infusion rate of 1 milligram per kilogram per day (mg/kg/24 hr), i.e., "1 mg/kg/24 hr" or of 3 mg/kg/24 hr, i.e., "3 mg/kg/24 hr". Data shown are means±SEM.

Statistics: Changes from baseline value were calculated for each time point using descriptive statistics (n, arithmetic mean, SD, CV). A comparison between active treatment and placebo was made for each time point and cohort using ANOVA with Dunnett's post-hoc correction of the p-value to account for multiple testing. Significance was set at p<0.05. Statistical analysis was executed using SAS software Version 9.4, Results & discussion: Subjects receiving the 5-HTP IV infusion at a constant flow rate had significantly higher plasma cortisol levels at 5-HTP infusion rates of 1 mg/kg/24 hr (p<0.01) and 3 mg/kg/24 hr (p<0.005) relative to placebo at the 2 hr time point after the start of infusion. See FIG. 4A. Plasma cortisol levels remained significantly higher in the 3 mg/kg/24 hr group relative to placebo throughout the 24 hr duration of the infusion, except at the 24 hr time point.

Subjects receiving the 5-HTP IV infusion at a ramp flow rate had significantly higher plasma cortisol levels at 5-HTP infusion rates of 2 mg/kg/24 hr (p<0.05) and 3 mg/kg/24 hr (p<0.0001) relative to placebo at the 14 hr time point after the start of infusion. See FIG. 4B. There was also a trend for higher plasma cortisol levels relative to placebo in subjects in the 1 mg/kg/24 hr cohort, but the increase was not statistically significant (p=0.0751). Thus, continuous IV administration of 5-HTP in the current study showed evidence of target engagement, elevations in extracellular serotonin beyond the SSRI effect.

REFERENCES

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

Attenburrow M J, Mitter P R, Whale R. Terao T, Cowen P J (2001). Low-dose citalopram as a 5-HT neuroendocrine probe. *Psychopharmacology* 155(3): 323-326.

Birdsall T C (1998). 5-Hydroxytryptophan: a clinically-effective serotonin precursor. *Altern Med Rev* 3(4): 271-280.

Bowsher R. R. HDP (1986). Aromatic L-Amino Acid Decarboxylase. In: Boulton A. A. BGB, Yu P. H. (ed). *Neurotransmitter Enzymes. Neuromethods (Series 1: Neurochemistry)*. Humana Press. Vol 5.

Demisch K. Demisch L, Bochnik H J, Nickelsen T, Althoff P H, Schoffling K, et al (1986). Melatonin and cortisol increase after fluvoxamine. *British journal of clinical pharmacology* 22(5): 620-622.

Dulay M S, Dulay J S (2020). Antiemetics: types, actions and uses. *Br J Hosp Med (Lond)* 81(5): 1-8.

Fu D J, Ionescu D F, Li X, Lane R, Lim P, Sanacora G. et al (2020). Esketamine Nasal Spray for Rapid Reduction of Major Depressive Disorder Symptoms in Patients Who Have Active Suicidal Ideation With Intent: Double-Blind, Randomized Study (ASPIRE I). *J Clin Psychiatry* 81(3).

Gibbons R D, Brown C H, Hur K, Davis J, Mann J J (2012). Suicidal thoughts and behavior with antidepressant treatment: reanalysis of the randomized placebo-controlled studies of fluoxetine and venlafaxine. *Arch Gen Psychiatry* 69(6): 580-587.

Gijsman H J, van Gerven J M, de Kam M L, Schoemaker R C, Pieters M S, Weemaes M. et al (2002). Placebo-controlled comparison of three dose-regimens of 5-hydroxytryptophan challenge test in healthy volunteers. *J Clin Psychopharmacol* 22(2): 183-189.

Guan Z, Jacobs G, van Pelt H, Van Gerven J M A, Burggraaf J, Zhao W (2020). PK/PD modeling of 5-hydroxytryptophan (5-HTP) challenge test with cortisol measurement in serum and saliva. *Pharmacol Res Perspect* 8(2): e00574.

Haahr M E, Fisher P M, Jensen C G, Frokjaer V G, Mahon B M, Madsen K. et al (2014). Central 5-HT4 receptor binding as biomarker of serotonergic tonus in humans: a [11C]SB207145 PET study. *Mol Psychiatry* 19(4): 427-432.

Jacobsen J P, Rudder M L, Roberts W, Royer E L, Robinson T J, Oh A. et al (2016a). SSRI Augmentation by 5-Hydroxytryptophan Slow Release: Mouse Pharmacodynamic Proof of Concept. *Neuropsychopharmacology* 41(9): 2324-2334.

Jacobsen J P R, Krystal A D, Krishnan K R R, Caron M G (2016b). Adjunctive 5-Hydroxytryptophan Slow-Release for Treatment-Resistant Depression: Clinical and Preclinical Rationale. *Trends Pharmacol Sci* 37(11): 933-944.

Kapitany T, Schindl M, Schindler S D, Hesselmann B, Fureder T, Barnas C, et al (1999). The citalopram challenge test in patients with major depression and in healthy controls. *Psychiatry Res* 88(2): 75-88.

Kelwala S. Stanley M, Gershon S (1983). History of antidepressants: successes and failures. *J Clin Psychiatry* 44(5 Pt 2): 40-48.

Levy A, Chen R (2016). Myoclonus: Pathophysiology and Treatment Options. *Curr Treat Options Neurol* 18(5): 21.

Lowe S L, Yeo K P, Teng L, Soon D K, Pan A. Wise S D, et al (2006). L-5-Hydroxytryptophan augments the neuroendocrine response to a SSRI. *Psychoneuroendocrinology* 31(4): 473-484.

Mashchak C A, Kletzky O A, Spencer C, Artal R (1983). Transient effect of L-5-hydroxytryptophan on pituitary function in men and women. *J Clin Endocrinol Metab* 56(1): 170-176.

Meltzer H Y, Uberkoman-Wiita B, Robertson A, Tricou B J, Lowy M (1983). Enhanced serum cortisol response to 5-hydroxytryptophan in depression and mania. *Life Sci* 33(25): 2541-2549.

Murphy T K, Segarra A, Storch E A, Goodman W K (2008). SSRI adverse events: how to monitor and manage. *International review of psychiatry* (Abingdon, England) 20(2): 203-208.

Nord M, Finnema S J, Halldin C, Farde L (2013). Effect of a single dose of escitalopram on serotonin concentration in the non-human and human primate brain. *Int J Neuropsychopharmacol* 16(7): 1577-1586.

Oquendo M A, Sullivan G M, Sudol K, Baca-Garcia E, Stanley B H, Sublette M E, et al (2014). Toward a biosignature for suicide. *Am. J Psychiatry* 171(12): 1259-1277.

Pereira V S, Hiroaki-Sato V A (2018). A brief history of antidepressant drug development: from tricyclics to beyond ketamine. *Acta Neuropsychiatr* 30(6): 307-322.

Rao N (2007). The clinical pharmacokinetics of escitalopram. *Clin Pharmacokinet* 46(4): 281-290.

Sargent P A, Williamson D J, Cowen P J (1998). Brain 5-HT neurotransmission during paroxetine treatment. *Br. J Psychiatry* 172: 49-52.

Smarius L J, Jacobs G E, Hoeberechts-Lefrandt D H, de Kam M L, van der Post J P, de Rijk R. et al (2008). Pharmacology of rising oral doses of 5-hydroxytryptophan with carbidopa. *J Psychopharmacol* 22(4): 426-433.

Smith B P, Vandenhende F R. DeSante K A, Farid N A, Welch P A, Callaghan J T, et al (2000). Confidence interval criteria for assessment of dose proportionality. *Pharm Res* 17(10): 1278-1283.

Tang S J, Nieto J M, Jensen D M, Ohning G V, Pisegna J R (2002). The novel use of an intravenous proton pump inhibitor in a patient with short bowel syndrome. *J Clin Gastroenterol* 34(1): 62-63.

Taylor M J, Freemantle N, Geddes J R, Bhagwagar Z (2006). Early onset of selective serotonin reuptake inhibitor antidepressant action: systematic review and meta-analysis. *Arch Gen Psychiatry* 63(11): 1217-1223.

Thombre A G (2005). Assessment of the feasibility of oral controlled release in an exploratory development setting. *Drug Discov Today* 10(17): 1159-1166.

Trivedi M H, Rush A J, Wisniewski S R, Nierenberg A A, Warden D, Ritz L, et al (2006). Evaluation of outcomes with citalopram for depression using measurement-based care in STAR*D: implications for clinical practice. *Am J Psychiatry* 163(1): 28-40.

Turner E H, Loftis J M, Blackwell A D (2006). Serotonin a la carte: supplementation with the serotonin precursor 5-hydroxytryptophan. *Pharmacol Ther* 109(3): 325-338.

van Hiele L J (1980). 1-5-Hydroxytryptophan in depression: the first substitution therapy in psychiatry? The treatment of 99 out-patients with 'therapy-resistant' depressions. *Neuropsychobiology* 6(4): 230-240.

van Vliet I M, Slaap B R, Westenberg H G, Den Boer J A (1996). Behavioral, neuroendocrine and biochemical effects of different doses of 5-HTP in panic disorder. *European neuropsychopharmacology: the journal of the European College of Neuropsychopharmacology* 6(2): 103-110.

Vigliante I, Mannino G, Maffei M E (2019). Chemical Characterization and DNA Fingerprinting of *Griffonia simplicifolia* Baill. *Molecules* 24(6).

Westenberg H G, Gerritsen T W, Meijer B A, van Praag H M (1982). Kinetics of 1-5-hydroxytryptophan in healthy subjects. *Psychiatry Res* 7(3): 373-385.

Yousefzadeh F, Sahebolzamani E. Sadri A, Mortezaei A, Aqamolaei A. Mortazavi S H. et al (2020). 5-Hydroxytryptophan as adjuvant therapy in treatment of moderate to severe obsessive-compulsive disorder: a double-blind randomized trial with placebo control. *Int Clin Psychopharmacol* 35(5): 254-262.

Zalsman G, Hawton K. Wasserman D, van Heeringen K, Arensman E, Sarchiapone M, et al (2016). Suicide prevention strategies revisited: 10-year systematic review. *Lancet Psychiatry* 3(7): 646-659.

U.S. Pat. No. 8,969,400.

U.S. Pat. No. 9,468,627.

U.S. Patent Application Publication No. 2021/0361566A1

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of elevating brain extracellular 5-hydroxytryptamine ($5\text{-HT}_{Ext}$) in a human subject in need thereof, wherein the method comprises administering 5-hydroxytryptophan (5-HTP) to the subject as a continuous intravenous (IV) infusion, wherein said continuous IV infusion comprises administering 5-HTP IV (a) at an average 5-HTP infusion rate of about 0.01 milligrams per kilogram bodyweight per hour (mg/kg/hr) to about 0.125 mg/kg/hr, and (b) for an infusion treatment period of about 4 hours or more; and wherein the method is free of administering a peripheral decarboxylase inhibitor (PDI) to the subject;

thereby providing a 5-HTP plasma exposure (i) defined as an area under the curve of a plasma concentration versus time curve extrapolated to infinity ($AUC_{Inf}$) and (ii) expressed in a unit of hours times nanograms per milliliter (h×ng/ml), predictable to be about the value calculated by the formula:

$$AUC_{Inf} = 3500 \times \text{IV dose of 5-HTP}$$

wherein the IV dose of 5-HTP is a total dose of 5-HTP administered over the infusion treatment period expressed in a unit of milligrams per kilogram (mg/kg).

2. The method of claim 1, wherein the 5-HTP infusion rate is constant throughout the infusion treatment period.

3. The method of claim 2, wherein the 5-HTP infusion rate is about 0.0417 mg/kg/hr and the administering provides a steady state 5-HTP plasma level of about 100 ng/ml.

4. The method of claim 2, wherein the 5-HTP infusion rate is about 0.0833 mg/kg/hr and the administering provides a steady state 5-HTP plasma level of about 200 ng/ml.

5. The method of claim 2, wherein the 5-HTP infusion rate is about 0.125 mg/kg/hr and the administering provides a steady state 5-HTP plasma level of about 300 ng/ml.

6. The method of claim 1, wherein the 5-HTP infusion rate is variable over the infusion treatment period.

7. The method of claim 6, wherein the continuous IV infusion is performed at a first 5-HTP infusion rate for a first portion of the infusion treatment period and at a second 5-HTP infusion rate for a second portion of the infusion treatment period, wherein the first 5-HTP infusion rate is lower than the second 5-HTP infusion rate.

8. The method of claim 1, wherein the infusion treatment period is about 4 hours to about 24 hours.

9. The method of claim 8, wherein the infusion treatment period is about 24 hours and the total dose of 5-HTP administered is about 1 mg/kg to about 3 mg/kg.

10. The method of claim 1, wherein the infusion treatment period is longer than 24 hours.

11. The method of claim 1, wherein the method further comprises administering to the subject a $5\text{-HT}_{Ext}$-elevating compound.

12. The method of claim 11, wherein the $5\text{-HT}_{Ext}$-elevating compound is a serotonin reuptake inhibitor and wherein the subject is being simultaneously treated with the serotonin reuptake inhibitor and/or has been pre-treated with the serotonin reuptake inhibitor.

13. The method of claim 1, wherein the administering provides an increase in plasma cortisol concentration in the subject compared to a subject not treated with the continuous IV infusion of 5-HTP.

14. The method of claim 1, wherein the method is free of severe and moderate adverse effects associated with administration of the continuous IV infusion of 5-HTP.

15. The method of claim 1, wherein the method further comprises administering to the subject an anti-emetic.

16. The method of claim 15, wherein the anti-emetic is a $5\text{-HT}_3$ receptor antagonist.

17. The method of claim 1, wherein the subject is a human in need of treatment for a neurological or psychiatric disorder.

18. The method of claim 17, wherein the neurological or psychiatric disorder is suicidal ideation or acute worsening of a mood disorder.

19. The method of claim 1, further comprising administering an additional treatment to the subject after completion of the infusion treatment period to maintain the therapeutic effect.

20. The method of claim 19, wherein the additional treatment comprises administration of a slow-release formulation including 5-HTP.

21. The method of claim 19, wherein administration of the additional treatment is initiated within about 24 hours of the completion of the infusion treatment period.

22. A method of providing a predictable 5-hydroxytryptophan (5-HTP) plasma exposure in a human subject, wherein the method comprises:
administering 5-hydroxytryptophan (5-HTP) to the subject as a continuous intravenous (IV) infusion, wherein the continuous IV infusion comprises administering 5-HTP IV (a) at an average 5-HTP infusion rate of about 0.01 milligrams per kilogram bodyweight per hour (mg/kg/hr) to about 0.125 mg/kg/hr, and (b) for an infusion treatment period of about 4 hours or more;
wherein said method is free of administering a peripheral decarboxylase inhibitor (PDI) to the subject;
thereby providing a 5-HTP plasma exposure (i) defined as an area under the curve of a plasma concentration versus time curve extrapolated to infinity ($AUC_{Inf}$) and (ii) expressed in a unit of hours times nanograms per milliliter (h×ng/ml), predictable to be about the value calculated by the formula:

$AUC_{Inf} = 3500 \times$ IV dose of 5-HTP wherein the IV dose of 5-HTP is a total dose of 5-HTP administered over the infusion treatment period expressed in a unit of milligrams per kilogram (mg/kg).

\* \* \* \* \*